US009802897B2

(12) United States Patent
Jeong et al.

(10) Patent No.: US 9,802,897 B2
(45) Date of Patent: Oct. 31, 2017

(54) AMIDOPYRIDINOL DERIVATIVE OR PHARMACEUTICALLY ACCEPTABLE SALT THEREOF AND PHARMACEUTICAL COMPOSITION COMPRISING SAME AS ACTIVE COMPONENT

(71) Applicant: Research Cooperation Foundation of Yeungnam University, Gyeongsangbuk-do (KR)

(72) Inventors: Byeong Seon Jeong, Daegu (KR); Jung Ae Kim, Daegu (KR); Tae gyu Nam, Gyeonggi-do (KR); Hyun Ji Lee, Daegu (KR); Dong Guk Kim, Daegu (KR); You Ra Kang, Daegu (KR); Jae Hui Been, Daegu (KR); You Jin Jin, Daegu (KR); Sushil Chandra Regmi, Gyeongsangbuk-do (KR); Jaya Gautam, Gyeongsangbuk-do (KR)

(73) Assignee: Research Cooperation Foundation of Yeungnam University, Gyeongsangbuk-do (KR)

( * ) Notice: Subject to any disclaimer, the term of this patent is extended or adjusted under 35 U.S.C. 154(b) by 0 days.

(21) Appl. No.: 14/784,957

(22) PCT Filed: Apr. 21, 2014

(86) PCT No.: PCT/KR2014/003450
§ 371 (c)(1),
(2) Date: Oct. 16, 2015

(87) PCT Pub. No.: WO2014/171801
PCT Pub. Date: Oct. 23, 2014

(65) Prior Publication Data
US 2016/0068489 A1 Mar. 10, 2016

(30) Foreign Application Priority Data

Apr. 19, 2013 (KR) .................. 10-2013-0043613
Apr. 17, 2014 (KR) .................. 10-2014-0046133
Apr. 17, 2014 (KR) .................. 10-2014-0046134
Apr. 17, 2014 (KR) .................. 10-2014-0046135

(51) Int. Cl.
C07D 213/75 (2006.01)
C07D 405/12 (2006.01)
C07D 409/12 (2006.01)

(52) U.S. Cl.
CPC ......... *C07D 213/75* (2013.01); *C07D 405/12* (2013.01); *C07D 409/12* (2013.01)

(58) Field of Classification Search
CPC .................................................. C07D 213/75
See application file for complete search history.

(56) References Cited

U.S. PATENT DOCUMENTS 4,672,070 A * 6/1987 Takahashi ............ A01N 43/40
514/346
8,569,336 B2 * 10/2013 Tong .................... C07D 498/04
514/269
2001/0039344 A1 11/2001 Bizzarro et al.

FOREIGN PATENT DOCUMENTS

WO 2009-012283 A1 1/2009

OTHER PUBLICATIONS

Moore et al. (Journal of the American Chemical Society (1959), 81, 6049-56).*
Fritz et al. (Helvetica Chimica Acta (1978), 61(8), 2887-98).*
Bolotin et al. (Khimiya Geterotsiklicheskikh Soedinenii (1992), (8), 1079-82). Abstract.*
International Search Report for PCT/KR2014/003450 dated Aug. 25, 2014 from Korean Intellectual Property Office.
Tipparaju, Suresh K. et al., Identification and Development of Novel Inhibitors of Toxoplasma gondii Enoyl Reductase, Journal of Medicinal Chemistry, 2010, pp. 6287-6300, vol. 53.
Serwa, Remigiusz et al., Preparation and Investigation of Vitamin B6-Derived Aminopyridinol Antioxidants, Chemistry—A European Journal, 2010, pp. 14106-14114, vol. 16.
D'Amato RJ et al., Mitomycin C versus 5, Fluorouracil in High,risk Glaucoma Filtering Surgery, Ophthalmology, vol. 102 (No. 9), pp. 1261-1262, 1995.
Arbiser JL, Angiogenesis and the skin: A primer, J. Am. Acad. Dermatol., 34(3), pp. 486-497, 1996.
Hanahan D et al., Patterns and Emerging Mechanisms of the Angiogenic Switch during Tumorigenesis, Cell, 86, pp. 353-364, 1996.
Koch AE et al., Stimulation of Neovascularization by Human Rheumatoid Synovial Tissue Macrophages, Arthritis. Rheum., 29, pp. 471-479, 1986.
Stupack DG et al., A role for angiogenesis in rheumatoid arthritis, Braz J. Med. Biol. Rcs., 32(5), pp. 578-581, 1999.
Koch AE, Angiogenesis in Arthritis, Atrhritis. Rheum., 41(6), pp. 951-962, 1998.
Jeffrey MI et al., Angiogenesis and vasculogenesis as therapeutic strategies for postnatal neovascularization, J. Clin. Invest., 103, pp. 1231-1236, 1999.

(Continued)

*Primary Examiner* — Bruck Kifle
(74) *Attorney, Agent, or Firm* — Revolution IP, PLLC

(57) ABSTRACT

An amidopyridinol derivative or a pharmaceutically acceptable salt thereof, and a pharmaceutical composition including the amidopyridinol derivative as an active component represented by Chemical Formula 1 or a pharmaceutically acceptable salt thereof have an antiangiogenic effect in a chorioallantoic membrane model, and thus are useful as an agent for preventing or treating diseases associated with angiogenesis, and also have a colitis-inhibitory effect in a model of inflammatory bowel diseases, and thus are useful as an agent for preventing or treating inflammatory bowel diseases. Upon inoculation of lung cancer cells in a chorioallantoic membrane model, the amidopyridinol derivative of Chemical Formula 1 or the pharmaceutically acceptable salt thereof inhibits angiogenesis and tumor growth that are caused by tumorigenesis, and also inhibits the activity of cathepsin S that plays an important role in metastasis and invasion of cancer, and thus is useful as an inhibitor of cancer growth and metastasis.

9 Claims, 10 Drawing Sheets

(56) References Cited

OTHER PUBLICATIONS

Adamis AP et al., Angiogenesis and ophthalmic disease, Angiogenesis, 3, pp. 9-14, 1999.
Folkman J, Angiogenesis in Psoriasis: Therapeutic Implications, J. Invest. Dermatol., 59, pp. 40-48, 1972.
Polverini PJ, The Pathophysiology of Angiogenesis, Crit. Rev. Oral. Biol. Med., 6(3), pp. 230-247, 1995.
Reiser J et al., Specialized roles for cysteine cathepsins in health and disease, J Clin Invest. 120(10), 3421-31, 2010.
Gormley JA et al., The role of Cathepsin S as a marker of prognosis and predictor of chemotherapy benefit in adjuvant CRC: a pilot study, Br J Cancer, 105(10), 1487-94, 2011.
Fan Q et al., Silencing cathepsin S gene expression inhibits growth, invasion and angiogenesis of human hepatocellular carcinoma in vitro, Biochem Biophys Res Commun, 425(4), 703-10, 2012.
Henry JA et al., Prognostic Significance of the Estrogen-Regulated Protein, Cathepsin D, in Breast Cancer, Cancer, 65 (2), 265-71, 1990.
Johnson MD et al., The Role of Cathepsin D in the Invasiveness of Human Breast Cancer Cells, Cancer Res., 53(4), 873-7, 1993.

\* cited by examiner

AMIDOPYRIDINOL DERIVATIVE OR PHARMACEUTICALLY ACCEPTABLE SALT THEREOF AND PHARMACEUTICAL COMPOSITION COMPRISING SAME AS ACTIVE COMPONENT

CROSS REFERENCE TO PRIOR APPLICATIONS

This application is the 35 U.S.C. 371 national stage of International application PCT/KR2014/003450 filed on Apr. 21, 2014; which claims priority to Korean Patent Application Nos. 10-2013-0043613 filed on Apr. 19, 2013, 10-2014-0046133 filed on Apr. 17, 2014, 10-2014-0046134 filed on Apr. 17, 2014, and 10-2014-0046135 filed on Apr. 17, 2014. The entire contents of each of the above-identified applications are hereby incorporated by reference.

TECHNICAL FIELD

The present invention relates to an amidopyridinol derivative or a pharmaceutically acceptable salt thereof, and a pharmaceutical composition including, as an active component, the amidopyridinol derivative or the pharmaceutically acceptable salt thereof, for preventing or treating diseases associated with angiogenesis, inflammatory bowel diseases, or cancer diseases.

BACKGROUND ART

Angiogenesis is a process through which new capillaries form from pre-existing microvessels. Angiogenesis may normally occur in the cases of embryonic development, tissue regeneration, wound healing, and development of corpus luteum in terms of changes in the periodic reproductive system of the female. In the cases described above, angiogenesis is strictly controlled to proceed.

Vascular endothelial cells for adults grow very slowly and do not divide relatively well compared to other types of cells. A process of angiogenesis generally consists of remodeling of blood vessels and generating of new capillaries through degradation of vascular basement membrane upon a protease that is stimulated by a stimulating factor, and tubular formation through movement, proliferation, and differentiation of vascular endothelial cells.

However, there are diseases caused when angiogenesis is not autonomously controlled, but becomes pathological. Diseases associated with angiogenesis in pathological conditions include hemangioma, angiofibroma, vascular malformation, and cardiovascular diseases, such as atherosclerosis, vascular adhesion, and scleroderma. Ophthalmologic diseases associated with angiogenesis include macular degeneration, corneal graft angiogenesis, neovascular glaucoma, diabetic retinopathy, corneal diseases associated with angiogenesis, macular degeneration, pterygium, retinal degeneration, retrolental fibroplasia, and trachoma. chronic inflammatoary diseases, such as arthritis, psoriasis, skin disease, such as capillarectasia, granuloma pyogenicum, seborrheic dermatitis, and acne, Alzheimer's disease, and obesity are also related to angiogenesis, and the growth of cancer and metastasis are definitely dependent upon angiogenesis (refer to D'Amato R J et al., *Ophthalmology*, 102(9), pp 1261-1262, 1995; Arbiser J L, *J. Am. Acad. Dermatol.*, 34(3), pp 486-497, 1996; O'Brien K D et al. *Circulation*, 93(4), pp 672-682, 1996; Hanahan D et al., *Cell*, 86, pp 353-364, 1996).

Arthritis, which is a representative inflammatory disease, is caused by autoimmune abnormalities, but due to pathological progression, chronic inflammation in a synovial cavity between joints may induce angiogenesis, thereby destroying cartilage. That is, by means of cytokines inducing inflammation, synovial and vascular endothelial cells are proliferated in the synovial cavity, leading to angiogenesis, and accordingly, the pannus junction, which is the connective tissue layer formed in the cartilage, thereby destroying the cartilage acting as a cushion (refer to Koch A E et al., *Arthritis. Rheum.*, 29, pp 471-479, 1986; Stupack D G et al., Braz *J. Med. Biol. Rcs.*, 32(5), pp 578-581, 1999; Koch A E, *Atrhritis. Rheum.*, 41(6), pp 951-962, 1998).

Many ophthalmologic diseases including blindness occurring in millions of worldwide people year after year are caused by angiogenesis (refer to Jeffrey M I et al., *J. Clin. Invest.*, 103, pp 1231-1236, 1999). Representative examples of diseases that are caused by angiogenesis include macular degeneration in the old, diabetic retinopathy, retinopathy of prematurity, neovascular glaucoma, and corneal diseases associated with angiogenesis (Adamis A P et al., *Angiogenesis*, 3, pp 9-14, 1999). In particular, diabetic retinopathy is a complication of diabetes, eventually being blinded due to invasion of the capillaries in the retina into the vitreous cavity.

Psoriasis characterized by redness and scaling skin is also a chronic proliferative disease occurring on the skin, but if not cured, psoriasis is accompanied by pain and deformity. Keratinocytes normally proliferate once a month, whereas keratinocytes in patients with psoriasis proliferate at least once a week. Since such rapid proliferation requires the supply of much blood, angiogenesis is actively bound to happen (Folkman J, *J. Invest. Dermatol.*, 59, pp 40-48, 1972).

In particular, in the case of cancer, angiogenesis plays an important role in the growth and metastasis of cancer cells. Tumors receive the supply of nutrients and oxygen necessary for the growth and proliferation through angiogenesis. In addition, new blood vessels infiltrated into tumors provide an opportunity for metastatic cancer cells to enter into the blood circulatory system, resulting in metastasis of the cancer cells (Folkman and Tyler, *Cancer Invasion and metastasis*, Biologic mechanisms and Therapy (S. B. Day ed.) Raven press, New York, pp 94-103, 1977; Polverini P J, *Crit. Rev. Oral. Biol. Med.*, 6(3), pp 230-247, 1995). The main cause of death in cancer patients is metastasis, and metastasis is the reason why chemotherapy and immunotherapy that are currently used in clinical trials fail to contribute to increasing the survival rates of cancer patients.

When looking at a metastasis process of most solid cancers, the process is carried out as follows: proliferation of cancer cells has been made in the first occurrence place of the cancer cells, and once a lump of the cancer cells gets larger, the cancer cells that are apart from the lump of the cancer cells to move to another location are moved through blood vessels and settled in a secondary place to allow the cell proliferation again. In the process, to move the cancer cells to another location through the blood vessels, the invasion of the cancer cells must occur. Here, to decompose extracellular matrix components, proteases are overexpressed by the cancer cells, and examples of the proteases include matrix metalloproteinases (MMPs), cathepsins, and various proteinases.

Cathepsin is a lysosome enzyme that breaks down proteins at a low pH, and may be classified into a serine protease (e.g., cathepsins A and G), an aspartyl protease (e.g., cathepsins D and E), and a cysterin protease (e.g., cathepsins B, C, F, H, K, L1, V, O, S, W, and Z). Cathepsin is involved in each specific physiological processes, and that is, cathepsin may be involved in antigen presentation in the immune system, collagen turnover between bonds and cartilages, and processing of neuropeptides and hormones. A lack of cathepsins causes various symptoms of diseases, and overexpression of cathepsin also causes a variety of diseases. In particular, it is known that overexpression of cysterin cathepsin (cathepsins B, F, H, K, L, V, S, and Z) is involved in cancer and metastasis (Reiser J et al., J Clin Invest. 120(10), 3421-31, 2010).

Cathepsin in most cases has a role as a ribosome protease in controlling a physiological function within a cell. As a protein that is secreted outside a cell and performs a proteolytic function, cathepsin S is disclosed. Cathepsin S in a cellular ribosome is involved in antibody processing or apoptosis, whereas cathepsin S secreted outside a cell breaks down extracellular matrix components, such as laminin, fibronectin, elastin, or collagen. It is deemed that, according to the functions above, cathepsin S is involved in the process of invasion of cancer cells and angiogenesis.

In a recent report, it is confirmed that expression of cathepsin S is significantly increased in a colorectal cancer tissue of a patient having colorectal cancer as compared with expression of cathepsin S in a normal colorectal tissue (refer to Gormley J A et al., Br J Cancer, 105(10), 1487-94, 2011). Furthermore, it has been reported that, when expression of cathepsin S is decreased by introducing siRNA, which targets a cathepsin S gene, to a liver cancer cell, a decrease in proliferation of the liver cancer cell, invasion of cancer, angiogenesis has been resulted (Fan Q et al., Biochem Biophys Res Commun, 425(4), 703-10, 2012).

In the case of breast cancer, prognosis of a patient having breast cancer metasized to lymphatic nodes is significantly related to cathepsin D staining in a breast cancer tissue cathepsin D, whereas cathepsin D is not related to a patient having non-metastatic lymphatic nodes (Henry J A et al., Cancer, 65(2), 265-71, 1990). On the basis of these results, it was suggested that cathepsin D played an important role in metastasis of breast cancer and invasion of cancer, but according to other studies on the same subject, it was resulted that, when breast cancer cell lines, such as MCF7, MDA-MB-231, and MDA-MB-435, were used to carry out experimental metastasis, cathepsin D had no relevance to invasion of breast cancer cells (Johnson M D et al., Cancer Res., 53(4), 873-7, 1993). As in the case of liver cancer, it is expected that cathepsin S may have important effects on metastatic breast cancer cells.

Also, inflammatory bowel disease (IBDs) is classified into two different diseases, i.e., ulcerative colitis and Crohn's disease, that is clinically similar with each other but are different from each other in terms of histological findings and endoscopic and immunological aspects. Such an IBD is known as a disease in which activation of inflammatory cells is important.

Sustained or inappropriate activation of the intestinal immune system plays an important role in pathological physiology of chronic mucosal inflammation, and more particularly, due to invasion of neutrophilic leukocytes, macrophages, lymphocytes, and mastocytes, mucosal destruction and ulcer are eventually caused. Neutrophilic leukocytes that are invaded and activated are considered as an important cause of active oxygen/nitrogen species, and such active species can induce a cellular oxidative stress upon a cytotoxic agent, such as cross-linked proteins, lipids, and nucleic acids, thereby causing epithelial dysfunction and damages.

When having inflammatory diseases, various inflammatory cytokines are secreted from the mucous membrane of the intestinal canal. TNF-α appears at a high level at a lumen of the large intestine and in intestinal epithelial cells of a patient having ulcerative colitis. According to recent studies, TNF-α is known to play an important role as a cause of ulcerative colitis. Infliximab, which is an anti-TNF-α antibody, is known to be effective in the treatment of not only boils, but also Crohn's disease that was not treated before. However, such treatment is expensive, and may cause side effects, such as transfusion reactions or infectious complications, in some patients.

Monocyte chemoattractant protein-1 (MCP-1) is a member of the C—C chemokine family having a molecular mass of 14 kDa, and mobilizes and activates mainly monocytes/macrophages in inflamed areas. MCP-1 is localized on epithelial cells of the large intestine, and it has been reported that the expression of MCP-1 is related to the invasion of monocytes in the mucous membrane of a patient having IBDs. Unlike other types of chemokines, MCP-1 binds to CCR2 only, and thus the binding of MCP-1/CCR2, as a main regulator of the mobilization of monocytes, is known to play an important role in IBDs.

In addition, interleukin 8 (IL-8) is known to be significantly increased in the mucous membrane of a patient having IBDs, thereby promoting capillary neovascularization. The more severe inflammation the large intestine has, the more the IL-8 is expressed. In addition, in an animal model using rodents, it is known that an antibody specific to the IL-8 reduces intestinal inflammation. Here, changes in intracellular $Ca^{2+}$ are regarded as important factors in the reduction of the IL-8.

As a therapeutic agent currently available for IBDs, 5-aminosalicylic acid (5-ASA)-based drugs that inhibit production of prostaglandins are used, and examples thereof are sulfasalazine and a steroidal immunosuppressant drug.

Sulfasalazine may cause side effects, such as fullness, headache, rash, liver diseases, leucopenia, agranulocytosis, or male infertility, or adverse effects. In addition, it is unclear whether sulfasalazine has sufficient inhibitory effects on the recurrence in patients having an incision on the affected part of the intestines to patients showing improvement.

A steroid immunosuppressant is an andrenocortical steroid and has acknowledged short-term effects. However, its long-term prognosis cannot be improved, and due to side effects including induced infectious disease, secondary adrenocortical insufficiency, peptic ulcers, diabetes, mental disorder, and steroidal kidney disease, there is a limitation that the steroid immunosuppressant drug should be used only in an acute situation.

Meanwhile, an angiogenesis inhibitor can be applied as a medicament for the treatment of such various diseases associated with angiogenesis or IBDs, or as an anti-cancer agent for preventing the growth of cancer and metastasis. Thus, recently, studies to treat the diseases described above by inhibiting angiogenesis are actively carried out.

DETAILED DESCRIPTION OF THE INVENTION

Technical Problem

In this regard, the present inventors have completed the present invention by confirming that an amidopyridinol derivative having a particular structure or a pharmaceutically acceptable salt of the amidopyridinol derivative have excellent inhibitory effects on angiogenesis, therapeutic effects on inflammatory bowel disease and cancer, and inhibitory effects on metastasis.

Thus, there is provided an amidopyridinol derivative or a pharmaceutically acceptable salt thereof.

Thus, there is provided a pharmaceutical composition including, as an active component, an amidopyridinol derivative or a pharmaceutically acceptable salt thereof.

Technical Solution

To achieve the e technical problems above, there is provided an amidopyridinol derivative represented by Chemical Formula 1 or a pharmaceutically acceptable salt thereof:

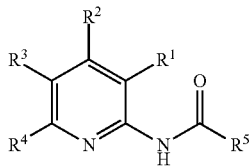

[Chemical Formula 1]

In Chemical Formula 1, $R^1$, $R^2$, and $R^4$ may be identical to or different from each other, and may each be one selected from hydrogen, C1-C4 alkyl, C1-C4 alkoxy, and halogen, $R^3$ may be one selected from C1-C4 alkoxy, benzyloxy, and hydroxy, $R^5$ may be one selected from C1-C15 alkyl substituted or not substituted with one or two substituents selected from halogen, hydroxy, C1-C12 alkoxy, phenoxy, C1-C12 alkylamino, C6-C14 aryl, and C1-C4 alkyl; C6-C14 aryl substituted or not substituted with one or two substituents selected from halogen, hydroxy, C1-C12 alkoxy, C1-C12 alkylamino, and C1-C4 alkyl; C2-C12 alkenyl substituted or not substituted with C6-C14 aryl; C3-C8 cycloalkyl; and C3-C14 heterocyclic compound.

In addition, there is provided pharmaceutical composition including, as an active component, an amidopyridinol derivative represented by Chemical Formula 1 above or a pharmaceutically acceptable salt thereof.

Advantageous Effects of the Invention

An amidopyridinol derivative or a pharmaceutically acceptable salt thereof according to the present invention may inhibit angiogenic growth by treating an angiogenesis inducer, such as a vascular endothelial growth factor (VEGF), in a chicken chorioallantoic membrane as an angiogenesis model. Accordingly, the amidopyridinol derivative or the pharmaceutically acceptable salt thereof according to the present invention may be useful as a medicament for preventing or treating a diseases associated with angiogenesis, such as macular degeneration and arthritis.

In addition, the amidopyridinol derivative or the pharmaceutically acceptable salt thereof according to the present invention may inhibit colitis in a model of inflammatory bowel diseases, and thus, may be useful as a medicament for prevention or treatment of inflammatory bowel diseases.

In addition, the amidopyridinol derivative or the pharmaceutically acceptable salt thereof according to the present invention may be useful as a medicament for inhibition of cancer growth and metastasis, since, after inoculating a chorioallantoic membrane model with lung cancer cells, angiogenesis upon tumor formation and tumor growth may be inhibited and activity of cathepsin S, which plays a key role in metastasis and invasion of cancer, may be also inhibited.

DESCRIPTION OF THE DRAWINGS

FIG. 7 shows changes in weights of the rat as being recorded every day from the first day to the sixth day of the administration of the amidopyridinol derivative, FIG. 8 is a view showing conditions of a large intestine that was observed with the naked eye, FIG. 9 is a view showing weights of a large intestine, and FIG. 10 is a view showing measurement of myeloperoxidase (MPO).

BEST MODE

Figure 1:
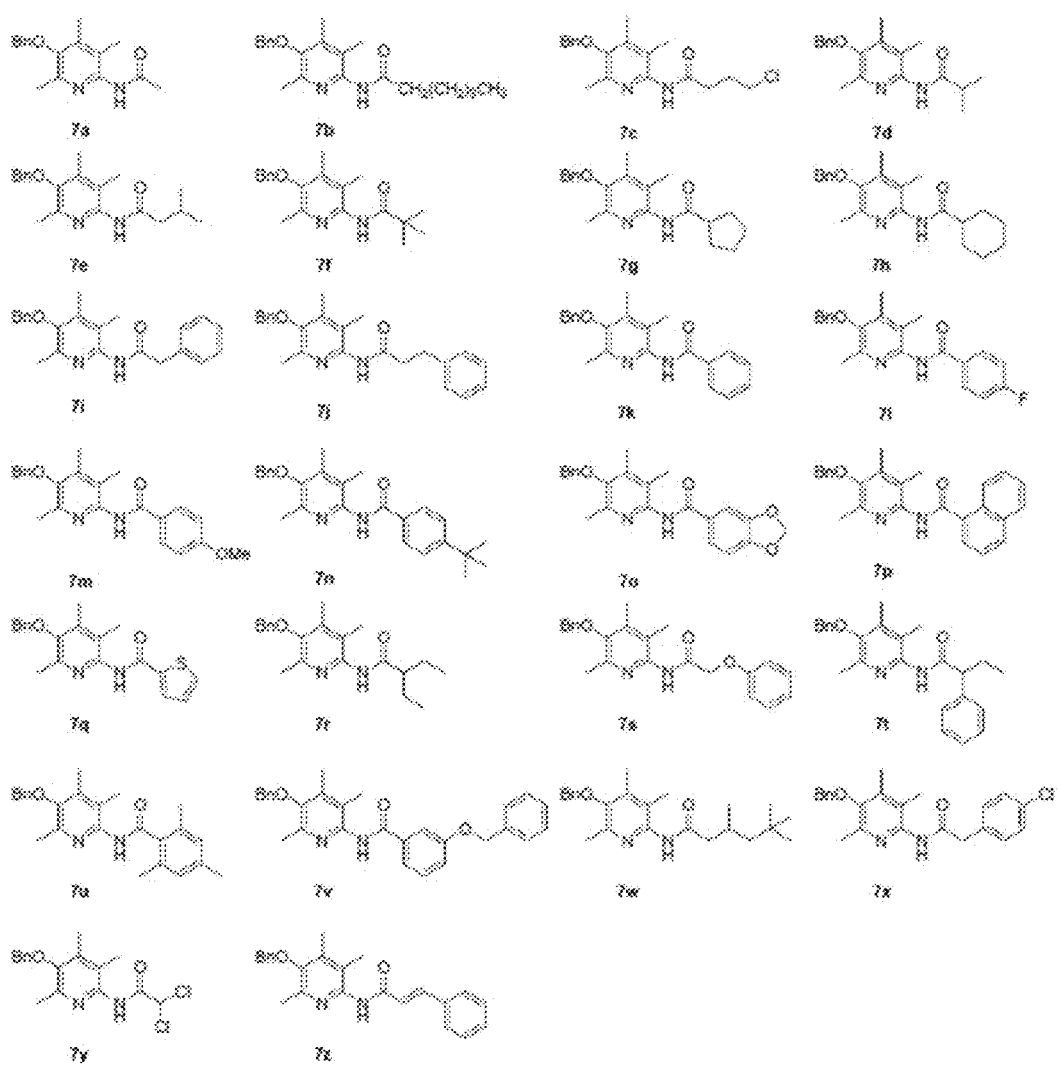
FIG. 1 is a view of amidopyridinol derivatives represented by Chemical Formula 1 according to an exemplary embodiment.

The present invention provides an amidopyridinol derivative represented by Chemical Formula 1 below or a pharmaceutically acceptable salt thereof

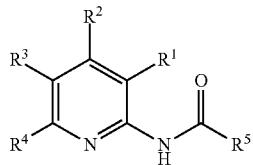

[Chemical Formula 1]

In Chemical Formula 1, $R^1$, $R^2$, and $R^4$ may be identical to or different from each other, and may be one selected from hydrogen, C1-C4 alkyl, C1-C4 alkoxy, and halogen, $R^3$ may be one selected from C1-C4 alkoxy, benzyloxy, and hydroxy, and $R^5$ may be one selected from C1-C15 alkyl substituted or not substituted with one or two substituents selected from halogen, hydroxy, C1-C12 alkoxy, phenoxy, C1-C12 alkylamino, C6-C14 aryl, and C1-C4 alkyl; C6-C14 aryl substituted or not substituted with one or two substituents selected from halogen, hydroxy, C1-C12 alkoxy, C1-C12 alkylamino, and C1-C4 alkyl; C2-C12 alkenyl substituted or not substituted with C6-C14 aryl; C3-C8 cycloalkyl; and C3-C14 heterocyclic compound.

In addition, the present invention provides a pharmaceutical composition for preventing or treating a disease associated with angiogenesis, the pharmaceutical composition including, as an active component, the amidopyridinol derivative of Chemical Formula 1 or the pharmaceutically acceptable salt thereof.

In addition, the present invention provides a pharmaceutical composition for treating or preventing an inflammatory bowel disease, the pharmaceutical composition including, as an active component, the amidopyridinol derivative of Chemical Formula 1 or the pharmaceutically acceptable salt thereof.

In addition, the present invention provides a pharmaceutical composition for preventing or treating cancer, the pharmaceutical composition including, as an active component, the amidopyridinol derivative of Chemical Formula 1 or the pharmaceutically acceptable salt thereof.

In addition, the present invention provides a pharmaceutical composition for preventing or inhibiting invasion of cancer or metastasis, the pharmaceutical composition including, as an active component, the amidopyridinol derivative of Chemical Formula 1 or the pharmaceutically acceptable salt thereof.

MODE OF THE INVENTION

Hereinafter, the present invention will be described in further detail.

The present invention provides an amidopyridinol derivative represented by Chemical Formula 1 below or a pharmaceutically acceptable salt thereof

[Chemical Formula 1]

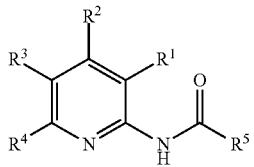

In Chemical Formula 1, $R^1$, $R^2$, and $R^4$ may be identical to or different from each other, and may be one selected from hydrogen, C1-C4 alkyl, C1-C4 alkoxy, and halogen, $R^3$ may be one selected from C1-C4 alkoxy, benzyloxy, and hydroxy, and $R^5$ may be one selected from C1-C15 alkyl substituted or not substituted with one or two substituents selected from halogen, hydroxy, C1-C12 alkoxy, phenoxy, C1-C12 alkylamino, C6-C14 aryl, and C1-C4 alkyl; C6-C14 aryl substituted or not substituted with one or two substituents selected from halogen, hydroxy, C1-C12 alkoxy, C1-C12 alkylamino, and C1-C4 alkyl; C2-C12 alkenyl substituted or not substituted with C6-C14 aryl; C3-C8 cycloalkyl; and C3-C14 heterocyclic compound.

Preferably, in the amidopyridinol derivative of Chemical Formula 1, $R^1$, $R^2$, and $R^4$ may be one selected from hydrogen, C1-C4 alkyl, and C1-C4 alkoxy, $R^3$ may be one selected from benzyloxy and hydroxy, $R^5$ may be one selected from C1-C15 alkyl substituted or not substituted with halogen or C1-C4 alkyl, phenyl substituted or not substituted with halogen, hydroxy, C1-C4 alkoxy or C1-C4 alkyl; C1-C4 alkyl substituted or not substituted with phenyl or halophenyl; cinnamyl; phenoxymethyl; C3-C8 cycloalkyl; benzodioxole; naphthalene; and thiophene.

More preferably, the amidopyridinol derivative may be one selected from N-(5-benzyloxy-3,4,6-trimethylpyridine-2-yl)amide derivative and N-(5-hydroxy-3,4,6-trimethylpyridine-2-yl)amide derivative.

The N-(5-benzyloxy-3,4,6-trimethylpyridine-2-yl)amide derivative may be one selected from the group consisting of N-(5-benzyloxy-3,4,6-trimethylpyridine-2-yl)acetamide, N-(5-benzyloxy-3,4,6-trimethylpyridine-2-yl)dodecanamide, N-(5-benzyloxy-3,4,6-trimethylpyridine-2-yl)-4-chlorobutanamide, N-(5-benzyloxy-3,4,6-trimethylpyridine-2-yl)isobutyrylamide, N-(5-benzyloxy-3,4,6-trimethylpyridine-2-yl)-3-methylbutanamide, N-(5-benzyloxy-3,4,6-trimethylpyridine-2-yl)pivalamide, N-(5-benzyloxy-3,4,6-trimethylpyridine-2-yl)cyclopentane carboxamide, N-(5-benzyloxy-3,4,6-trimethylpyridine-2-yl)cyclohexane carboxamide, N-(5-benzyloxy-3,4,6-trimethylpyridine-2-yl)-2-penylacetamide, N-(5-benzyloxy-3,4,6-trimethylpyridine-2-yl)-3-phenylpropanamide, N-(5-benzyloxy-3,4,6-trimethylpyridine-2-yl)benzamide, N-(5-benzyloxy-3,4,6-trimethylpyridine-2-yl)-4-fluorobenzamide, N-(5-benzyloxy-3,4,6-trimethylpyridine-2-yl)-4-methoxybenzamide, N-(5-benzyloxy-3,4,6-trimethylpyridine-2-yl)-4-(tert-butyl)benzamide, N-(5-benzyloxy-3,4,6-trimethylpyridine-2-yl)benzo[d][1,3]dioxol-5-carboxamide, N-(5-benzyloxy-3,4,6-trimethylpyridine-2-yl)-1-naphthamide, N-(5-benzyloxy-3,4,6-trimethylpyridine-2-yl)thiophene-2-carboxamide, N-(5-benzyloxy-3,4,6-trimethylpyridine-2-yl)-2-ethylbutanamide, N-(5-benzyloxy-3,4,6-trimethylpyridine-2-yl)-2-phenoxyacetamide, N-(5-benzyloxy-3,4,6-trimethylpyridine-2-yl)-2-phenylbutanamide, N-(5-benzyloxy-3,4,6-trimethylpyridine-2-yl)-2,4,6-trimethylbenzamide, 3-benzyloxy-N-(5-benzyloxy-3,4,6-trimethylpyridine-2-yl)benzamide, N-(5-benzyloxy-3,4,6-trimethylpyridine-2-yl)-3,5,5-trimethylhexanamide, N-(5-benzyloxy-3,4,6-trimethylpyridine-2-yl)-2-(4-chlorophenyl)acetamide, N-(5-benzyloxy-3,4,6-trimethylpyridine-2-yl)-2,2-dichloroacetamide, and N-(5-benzyloxy-3,4,6-trimethylpyridine-2-yl)cinnamide.

The N-(5-hydroxy-3,4,6-trimethylpyridine-2-yl)amide derivative may be one selected from the group consisting of N-(5-hydroxy-3,4,6-trimethylpyridine-2-yl)acetamide, N-(5-hydroxy-3,4,6-trimethylpyridine-2-yl)dodecanamide, N-(5-hydroxy-3,4,6-trimethylpyridine-2-yl)-4-chlorobutanamide, N-(5-hydroxy-3,4,6-trimethylpyridine-2-yl)isobutyrylamide, N-(5-hydroxy-3,4,6-trimethylpyridine-2-yl)-3-methylbutanamide, N-(5-hydroxy-3,4,6-trimethylpyridine-2-yl)pivalamide, N-(5-hydroxy-3,4,6-trimethylpyridine-2-yl)cyclopentane carboxamide, N-(5-hydroxy-3,4,6-trimethylpyridine-2-yl)cyclohexane carboxamide, N-(5-hydroxy-3,4,6-trimethylpyridine-2-yl)-2-penylacetamide, N-(5-hydroxy-3,4,6-trimethylpyridine-2-yl)-3-phenylpropanamide, N-(5-hydroxy-3,4,6-trimethylpyridine-2-yl)benzamide, N-(5-hydroxy-3,4,6-trimethylpyridine-2-yl)-4-fluorobenzamide, N-(5-hydroxy-3,4,6-trimethylpyridine-2-yl)-4-methoxybenzamide, N-(5-hydroxy-3,4,6-trimethylpyridine-2-yl)-4-(tert-butyl)benzamide, N-(5-hydroxy-3,4,6-trimethylpyridine-2-yl)benzo[d][1,3]dioxol-5-carboxamide, N-(5-hydroxy-3,4,6-trimethylpyridine-2-yl)-1-naphthamide, N-(5-hydroxy-3,4,6-trimethylpyridine-2-yl)thiophene-2-carboxamide, 2-ethyl-N-(5-hydroxy-3,4,6-trimethylpyridine-2-yl)butanamide, N-(5-hydroxy-3,4,6-trimethylpyridine-2-yl)-2-phenoxyacetamide, N-(5-hydroxy-3,4,6-trimethylpyridine-2-yl)-2-phenylbutanamide, N-(5-hydroxy-3,4,6-trimethylpyridine- 2-yl)-2,4,6-trimethylbenzamide, 3-hydroxy-N-(5-hydroxy-3,4,6-trimethylpyridine-2-yl)benzamide, N-(5-hydroxy-3,4,6-trimethylpyridine-2-yl)-3,5,5-trimethylhexanamide, 2-(4-chlorophenyl)-N-(5-hydroxy-3,4,6-trimethylpyridine-2-yl)acetamide, 2,2-dichloro-N-(5-hydroxy-3,4,6-trimethylpyridine-2-yl)acetamide, and N-(5-hydroxy-3,4,6-trimethylpyridine-2-yl)cinnamide.

The pharmaceutically acceptable salt of the amidopyridinol derivative may be an organic acid selected from the group consisting of oxalic acid, maleic acid, fumaric acid, malic acid, tartaric acid, citric acid, and benzoic acid, or may be in the form of an acid addition salt produced by an inorganic acid selected from the group consisting of hydrochloric acid, sulfuric acid, phosphoric acid, and hydrobromic acid.

The amidopyridinol derivative of Chemical Formula 1 and the pharmaceutically acceptable salt thereof according to the present invention may be prepared according to a preparation method represented by Equation 1 below:

[Equation 1]

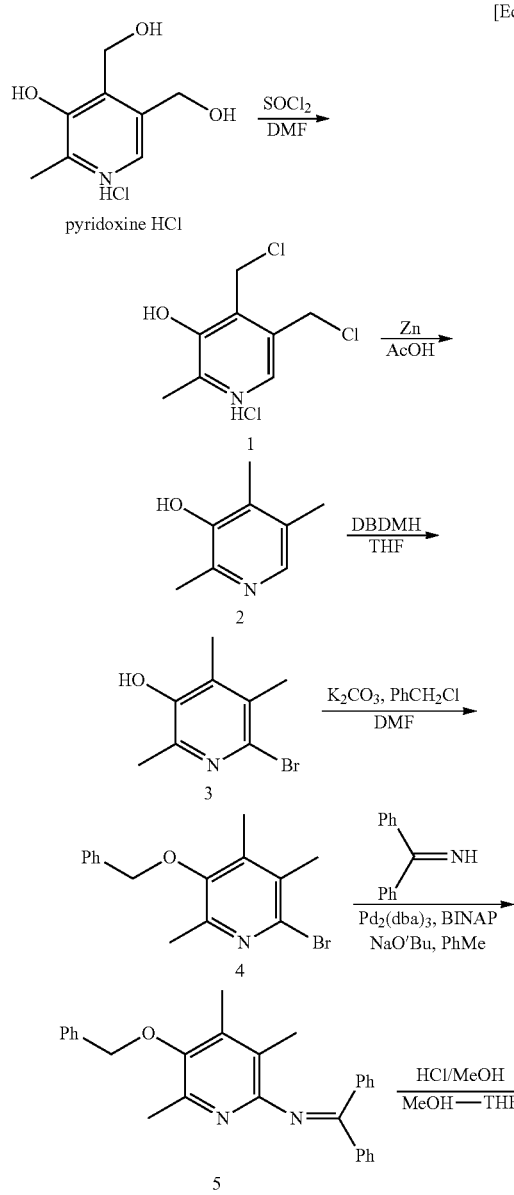

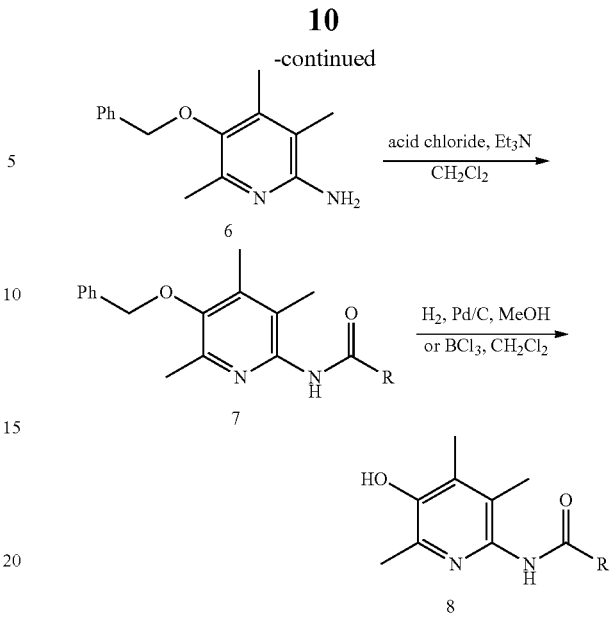

In more detail, $SOCl_2$ and dimethylformamide (DMF) were added to pyridoxine hydrochloride, and were stirred at reflux, so as to obtain Compound 1. Then, a small amount of zinc powder was added to a reaction solution in which Compound 1 was suspended with acetic acid, and the mixed solution was stirred at reflux, so as to obtain Compound 2. Then, 1,3-dibromo-5,5-dimethylhydantoin (DBDMH) was added to a reaction solution in which Compound 2 was suspended with tetrahydrofuran (THF), and the mixed solution was stirred at reflux, so as to obtain Compound 3. Then, $K_2CO_3$ and benzyl chloride ($PhCH_2Cl$) were added to a reaction solution in which Compound 3 was dissolved in DMF, so as to obtain Compound 4. Then, benzophenone imine was added to a reaction solution in which Compound 4, NaO$^t$Bu, tri(dibenzylideneacetone)dipalladium ($Pd_2(dba)_3$), and 2,2'-bis(diphenylphosphino)-1,1'-binaphthyl (BINAP) were dissolved in toluene, and the mixed solution was stirred at reflux, so as to obtain Compound 5. Then, a methanol solution containing a small amount of acetyl chloride was added to a reaction solution in which Compound 5 was dissolved in a mixed solvent of methanol and THF, and the mixed solution was stirred at reflux, so as to obtain Compound 6. Then, to triethylamine and acetyl chloride were sequentially added to a reaction solution in which Compound 6 was dissolved in $CH_2Cl_2$, and the mixed solution was stirred, so as to obtain Compound 7. In addition, Pd/C was added to a reaction solution in which Compound 7 was dissolved in methanol, and the mixed solution was stirred under a hydrogen atmosphere, so as to obtain Compound 8. Alternatively, $BCl_3$ was added to a reaction solution in which Compound 7 was dissolved in $CH_2Cl_2BCl_3$, so as to obtain Compound 8.

In addition, the present invention provides a pharmaceutical composition for preventing or treating a disease associated with angiogenesis, the pharmaceutical composition including, as an active component, the amidopyridinol derivative of Chemical Formula 1 or the pharmaceutically acceptable salt thereof.

The disease associated with angiogenesis may be an ophthalmologic disease selected from macular degeneration, diabetic retinopathy, proliferative vitreoretinopathy, immature retinopathy, glaucoma, degeneration, pterygium, retrolental fibroplasia, trachoma, rejection of corneal transplantation, corneal ulcer, conical cornea, and ophthalmic inflammation.

The disease associated with angiogenesis may be one selected from rheumatoid arthritis, osteoarthritis, septic arthritis, psoriasis, Siogren's syndrome, abnormal cut conglutination, bone disease, albuminuria, abdominal aortic aneurysm, degenerative cartilage loss resulting from traumatic joint damage, neurologic demyelination, cirrhosis, glomerular disease, immature rupture of embryo-fetal membrane, periodontal diseases, atherosclerosis, restenosis, inflammatory diseases of the central nervous system, Alzheimer's disease, and skin aging.

The amidopyridinol derivative or the pharmaceutically acceptable salt thereof according to the present invention inhibits angiogenic growth by treating an angiogenesis inducer, such as a vascular endothelial growth factor (VEGF), in a chicken chorioallantoic membrane as an angiogenesis model. Accordingly, the amidopyridinol derivative or the pharmaceutically acceptable salt thereof according to the present invention may be useful as a medicament for preventing or treating a diseases associated with angiogenesis, such as macular degeneration and arthritis.

In addition, the prevent invention provides a pharmaceutical composition for preventing or treating an IBD, the pharmaceutical composition including, as an active component, an amidopyridinol derivative represented by Chemical Formula 1 or a pharmaceutically acceptable salt thereof.

The IBD may be selected from the group consisting of ulcerative colitis, Crohn's disease, intestinal Behcet's disease, hemorrhagic rectal ulcer, and pouchitis.

The amidopyridinol derivative or the pharmaceutically acceptable salt thereof according to the present invention has an excellent colitis-inhibitory effect in a model of IBDs, and thus, may be useful as an agent for preventing or treating IBDs.

In addition, the prevent invention provides a pharmaceutical composition for preventing or treating a cancer disease, the pharmaceutical composition including, as an active component, an amidopyridinol derivative represented by Chemical Formula 1 or a pharmaceutically acceptable salt thereof.

In addition, the prevent invention provides a pharmaceutical composition for preventing or inhibiting invasion of cancer or metastasis, the pharmaceutical composition including, as an active component, an amidopyridinol derivative represented by Chemical Formula 1 or a pharmaceutically acceptable salt thereof.

The cancer disease may be one selected from the group consisting of lung cancer, breast cancer, bladder cancer, bone cancer, thyroid cancer, parathyroid cancer, rectal cancer, laryngopharyngeal cancer, larynx cancer, esophageal cancer, pancreatic cancer, colon cancer, stomach cancer, tongue cancer, skin cancer, brain cancer, uterine cancer, head or neck cancer, gallbladder cancer, oral cancer, colon cancer, anal cancer, tumors of the central nervous system, and liver cancer.

Upon inoculation of lung cancer cells in a chorioallantoic membrane model, the amidopyridinol derivative of Chemical Formula 1 or the pharmaceutically acceptable salt thereof inhibits angiogenesis and tumor growth that are caused by tumorigenesis, and also inhibits the activity of cathepsin S that plays an important role in metastasis and invasion of cancer, and thus is useful as an inhibitor of cancer growth and metastasis.

An application amount of and a method of applying the pharmaceutical composition according to the present invention may differ depending on formulation and usage of the pharmaceutical composition.

The pharmaceutical composition according to the present invention may include the amidopyridinol derivative or the pharmaceutically acceptable salt thereof in an amount ranging from about 0.1 to about 50 weight % based on the total weight of pharmaceutical composition.

In addition, the pharmaceutical composition according to the present invention may further include an appropriate carrier, excipient, and diluents that are typically used in the preparation of the pharmaceutical composition.

Examples of the carrier, excipient, and the diluents include lactose, dextrose, sucrose, sorbitol, mannitol, zylitol, erythritol, maltitol, starch, acacia rubber, alginate, gelatin, calcium phosphate, calcium silicate, cellulose, methyl cellulose, microstalline cellulose, polyvinylpyrrolidone, water, methylhydroxy benzoate, propylhydroxy benzoate, talc, magnesium stearate, and mineral oil.

The pharmaceutical composition according to the present invention may be formulated in oral formulations, such as powders, granules, tablets, capsules, suspensions, emulsions, syrups, and aerosols, or may be formulated in the form of external application, suppositories, and sterile injectable solutions, each according to typical methods in the art.

When formulated, typical diluents or excipients, such as fillers, extenders, binders, wetting agents, disintegrating agents, and surfactants may be used. Examples of solid formulations for oral administration include tablets, pills, powders, granules, and capsules, and these solid formulations are prepared by mixing with at least one excipient, such as starch, calcium carbonate, sucros or lactose, or gelatin.

Also, lubricants, such as magnesium stearate and talc, may be used in addition to simple exicpient. Examples of liquid formulations for oral administration include suspension, solutions, emulsions, and syrups. In addition to simple diluents that are commonly used, such as water or liquid paraffin, liquid formulations may also include various excipients, e.g., wetting agents, sweeteners, aromatics, and preservatives. Examples of formulations for parenteral administration include sterilized aqueous solutions, non-aqueous solvents, suspensions, emulsions, lyophilized preparations, and suppositories. Examples of the non-aqueous solvent and the suspensions include propylene glycol, polyethylene glycol, vegetable oil, such as olive oil, and injectable ester, such as ethyl oleate. Examples of suppository bases include witepsol, macrogol, tween 61, cacao butter, laurin, and glycerol geletin.

The amidopyridinol derivative or the pharmaceutically acceptable salt thereof according to the present invention may differ depending on a patient's age, gender, or weight, but for example, may be administered to a patient in a dosage ranging from about 0.001 to about 100 mg/kg, preferable, about 0.01 to about 10 mg/kg, once a day or several times a day. In addition, a dosage of the amidopyridinol derivative or the pharmaceutically acceptable salt thereof may be increased or decreased according to an administration route, severity of a disease, or a patient's gender, weight, or age. Thus, the dosage is not construed to limit the scope of the present invention in any aspect.

The pharmaceutical composition may be administered to a mammal by a variety of routes, and examples of the mammal include rats, mice, cattle, and humans. All the administration routes may be expected, and for example, the pharmaceutical composition may be administered by oral, rectal or intravenous, muscle, subcutaneous, or intrauterine or intracerebroventricular injection.

The amidopyridinol derivative or the pharmaceutically acceptable salt according to the present invention has a lethal dose 50% ($LC_{50}$) of at least 2 g/kg, thereby securing the stability. Thus, the amidopyridinol derivative or the pharmaceutically acceptable salt according to the present invention may be applied to the pharmaceutical composition.

Hereinafter, the present invention is further illustrated by the following examples and comparative examples. However, it shall be understood that these examples are only used to specifically set forth the present disclosure, and they are not limited in any form.

EXAMPLE 1

Preparation of 4,5-bis(chloromethyl)-2-methylpyridine-3-ol hydrochloride (1)

30 mL of thionyl chloride and 0.2 mL of DMF (2.583 mmol) were added to 5 g (24.31 mmol) of pyridoxin hydrochloride, and then, the mixed solution was stirred at 80° C. for 3 hours under reflux. After the reaction solution was cooled to room temperature, 70 ml of ethyl ether was added thereto, and the mixed solution was stirred for 1 hour under ice-cooling. Precipitated solids were subjected to vacuum filtration, and the filtered solids were washed with ethyl ether, and then, dried, thereby obtaining 5.5 g of white solids, i.e., Compound 1 (yield: 93%).

$^1$H-NMR (250 MHz, DMSO-$d_6$) δ 8.42 (s, 1H), 4.99 (s, 2H), 4.96 (s, 2H), 2.63 (s, 3H) ppm

EXAMPLE 2

Preparation of 2,4,5-trimethylpyridine-3-ol (2)

8.08 g (123.69 mmol) of zinc powders was sub-divided into 50 ml of acetic acid suspension containing 10 g (41.23 mmol) of Compound 1, and then, the mixed solution was stirred at 130° C. for 2 hours under reflux. After being cooled to room temperature, the reaction solution was subjected to vacuum filtration. Then, a 10 M NaOH solution was used to adjust a pH of the filtrate to 6. The filtrate was saturated with salts, and was extracted with EtOAc solution (100 mL×6). The EtOAc solution was washed with saturated brine, dried with anhydrous $MgSO_4$, filtered, and then, concentrated under reduced pressure. The residues were purified by column chromatography ($CHCl_3$:MeOH=20:1), thereby obtaining 5.2 g (92%) of white solids, i.e., Compound 2.

$^1$H-NMR (250 MHz, DMSO-$d_6$) δ 8.49 (s, 1H), 7.72 (s, 1H), 2.31 (s, 3H), 2.12 (s, 3H), 2.08 (s, 3H) ppm

EXAMPLE 3

Preparation of 6-bromo-2,4,5-trimethylpyridine-3-ol (3)

2.5 g (9.11 mmol) of 1,3-dibromo-5,5-dimethylhydantoin (DBDMH) was added to 30 mL of a THF suspension solution containing 2.5 g (18.22 mmol) of Compound 2, and then, the mixed solution was stirred at room temperature for 3 hours. After the reaction solution was concentrated, the residues were diluted with 500 mL of EtOAc solution and 20 mL of water, and then, an aqueous layer was extracted with EtOAc (100 mL×3). The EtOAc solution was washed with saturated brine, dried with anhydrous $MgSO_4$, filtered, and then, concentrated under reduced pressure. The residues were purified by column chromatography (EtOAc: Hex=1:4), thereby obtaining 3.22 (80%) of pale yellow solids, i.e., Compound 3.

$^1$H-NMR (250 MHz, $CHCl_3$-d) δ 5.56 (br s, 1H), 2.42 (s, 3H), 2.31 (s, 3H), 2.25 (s, 3H) ppm

EXAMPLE 4

Preparation of 3-(benzyloxy)-6-bromo-2,4,5-trimethylpyridine (4)

20.78 g (150.04 mmol) of $K_2CO_3$ and 5.2 mL (45.12 mmol) of benzyl chloride were sequentially added to 15 mL of DMF containing 6.5 g (30.08 mmol) of Compound 3, and the mixed solution was stirred at room temperature for 12 hours. The reaction solution was diluted with 700 mL of EtOAc, and then, washed with water (20 mL×10). The EtOAc solution was washed with saturated brine, dried with anhydrous $MgSO_4$, filtered, and then, concentrated under reduced pressure. The residues were purified by column chromatography (EtOAC:Hex=1:20), thereby obtaining 8.9 g (97%) of white solids, i.e., Compound 4.

$^1$H-NMR (250 MHz, $CHCl_3$-d) δ 7.38-7.43 (m, 5H), 4.77 (s, 2H), 2.46 (s, 3H), 2.32 (s, 3H), 2.24 (s, 3H) ppm

EXAMPLE 5

Preparation of 5-(benzyloxy)-N-(diphenylmethylene)-3,4,6-trimethylpyridine-2-amine (5)

1.73 mL (9.80 mmol) of benzophenone imine was added to 30 ml of a toluene solution containing 3 g (9.80 mmol) of Compound 4, 203 mg (0.20 mmol) of tris(dibenzylideneacetone)dipalladium(0) ($Pd_2(DBA)_3$), 249 mg (0.39 mmol) of 2,2'-bis(diphenylphosphino)-1,1'-binaphthyl (BINAP), and 1.36 g (13.71 mmol) of NaO$^t$Bu, and then, the mixed solution was stirred at 120° C. for 12 hours under reflux. After being cooled to room temperature, the reaction solution was diluted with 700 mL of EtOAc and 10 mL of water. Then, the EtOAc solution was washed with saturated brine (30 mL×5), dried with anhydrous $MgSO_4$, filtered, and then, concentrated under reduced pressure. The residues were purified by column chromatography (EtOAc:Hex=1:4), thereby obtaining 3.28 g (83%) of yellow solids, i.e., Compound 5.

$^1$H-NMR (250 MHz, $CHCl_3$-d) δ 7.80 (d, J=7.1 Hz, 2H), 7.17-7.48 (m, 13H), 4.69 (s, 2H), 2.29 (s, 3H), 2.03 (s, 3H), 1.91 (s, 3H) ppm

EXAMPLE 6

Preparation of 5-(benzyloxy)-3,4,6-trimethylpyridine-2-amine (6)

2 mL of acetyl chloride was slowly added dropwise to be dissolved in 50 mL of methanol under ice-cooling. The mixed solution was added to a solution of Compound 5 containing 50 mL of methanol and 5 mL of THT, and then, the mixed solution was stirred at room temperature for 12 hours. The reaction solution that was concentrated under pressure was diluted with 300 mL of EtOAc, and then, washed with saturated sodium hydrogencarbonate aqueous solution (20 mL×4). The EtOAc solution was washed with 20 mL of satured brine, dried with anhydrous $MgSO_4$, filtered, and then, concentrated under reduced pressure. The residues were purified by column chromatography ($CHCl_3$:

MeOH=20:1), thereby obtaining 992 mg (83%) of pale yellow solids, i.e., Compound 6.

$^1$H-NMR (250 MHz, CHCl$_3$-d) δ 7.31-7.45 (m, 5H), 4.68 (s, 2H), 4.25 (br s, 1H), 2.34 (s, 3H), 2.16 (s, 3H), 1.99 (s, 3H) ppm

EXAMPLE 7

Preparation of N-(5-benzyloxy-3,4,6-trimethylpyridine-2-yl)amide derivatives (7a-7z)

N-(5-benzyloxy-3,4,6-trimethylpyridine-2-yl)amide derivatives each prepared in the following manners are shown in FIG. 1.

EXAMPLE 7-1

Preparation of N-(5-benzyloxy-3,4,6-trimethylpyridine-2-yl)acetamide (7a)

0.161 mL (1.155 mmol) of triethylamine and 0.073 mL (0.990 mmol) of acetyl chloride were sequentially added to 5 mL of CH$_2$Cl$_2$ containing 200 mg (0.825 mmol) of Compound 6, and then, the mixed solution was stirred at room temperature for 8 hours. The reaction solution was diluted with 100 mL of CH$_2$Cl$_2$, and then washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=2:1), thereby obtaining 184 mg (78%) of yellow solids. i.e., Compound 7a.

$^1$H-NMR (250 MHz, CHCl$_3$-d) δ 8.44 (br s, 1H), 7.30-7.45 (m, 5H), 4.75 (s, 2H), 2.40 (s, 3H), 2.23 (s, 3H), 2.16 (s, 3H), 2.13 (s, 3H) ppm

EXAMPLE 7-2

Preparation of N-(5-benzyloxy-3,4,6-trimethylpyridine-2-yl)dodecanamide (7b)

0.120 mL (0.867 mmol) of triethylamine and 0.176 mL (0.743 mmol) of dodecanoyl chloride were sequentially added to 5 mL of CH$_2$Cl$_2$ containing 150 mg (0.619 mmol) of Compound 6, and then, the mixed solution was stirred at room temperature for 5 hours. The reaction solution was diluted with 100 mL of CH$_2$Cl$_2$, and then washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 184 mg (70%) of white solids, i.e., Compound 7b.

$^1$H-NMR (250 MHz, CHCl$_3$-d) δ 7.74 (br s, 1H), 7.35-7.46 (m, 5H), 4.76 (s, 2H), 2.41 (s, 3H), 2.35-2.40 (m, 2H), 2.23 (s, 3H), 2.11 (s, 3H), 1.65-1.77 (m, 2H), 1.25 (s, 16H), 0.86 (t, J=6.8 Hz, 3H) ppm

EXAMPLE 7-3

Preparation of N-(5-benzyloxy-3,4,6-trimethylpyridine-2-yl)-4-chlorobutanamide (7c)

0.688 mL (2.475 mmol) of triethylamine and 1.155 mL (2.887 mmol) of 4-chlorobutanoyl chloride were sequentially added to 100 mL of CH$_2$Cl$_2$ containing 500 mg (2.063 mmol) of Compound 6, and then, the mixed solution was stirred at room temperature for 5 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:1), thereby obtaining 102 mg (14%) of white solids, i.e., Compound 7c.

$^1$H-NMR (250 MHz, CHCl$_3$-d) δ 8.37 (br s, 1H), 7.33-7.44 (m, 5H), 4.76 (s, 2H), 3.63 (t, J=6.3 Hz, 2H), 2.59 (t, J=7.1 Hz, 2H), 2.41 (s, 3H), 2.23 (s, 3H), 2.16 (t, J=6.8 Hz, 2H), 2.11 (s, 3H) ppm

EXAMPLE 7-4

Preparation of N-(5-benzyloxy-3,4,6-trimethylpyridine-2-yl)isobutyrylamide (7d)

0.161 mL (1.155 mmol) of triethylamine and 107 mg (0.990 mmol) of isobutyryl chloride were sequential added to 100 mL of CH$_2$Cl$_2$ containing 200 mg (0.825 mmol) of Compound 6, and then, the mixed solution was stirred at room temperature for 5 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:3), thereby obtaining 177 mg (72%) of white solids, i.e., Compound 7d.

$^1$H-NMR (250 MHz, CHCl$_3$-d) δ 8.51 (br s, 1H), 7.34-7.47 (m, 5H), 4.75 (s, 2H), 2.56-2.67 (m, 1H), 2.41 (s, 3H), 2.24 (s, 3H), 2.09 (s, 3H), 1.25 (s, 3H), 1.22 (s, 3H) ppm

EXAMPLE 7-5

Preparation of N-(5-benzyloxy-3,4,6-trimethylpyridine-2-yl)-3-methylbutanamide (7e)

0.161 mL (1.155 mmol) of triethylamine and 0.124 mL (0.990 mmol) of isovaleryl chloride were sequentially added to 10 mL of CH$_2$Cl$_2$ containing 200 mg (0.825 mmol) of Compound 6, and then, the mixed solution was stirred at room temperature for 5 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:3), thereby obtaining 197 mg (73%) of white solids, i.e., Compound 7e.

$^1$H-NMR (250 MHz, CHCl$_3$-d) δ 8.59 (br s, 1H), 7.31-7.45 (m, 5H), 4.74 (s, 2H), 2.40 (s, 3H), 2.24-2.25 (m, 6H), 2.12 (s, 3H), 1.00 (d, J=6.3 Hz, 6H) ppm

EXAMPLE 7-6

Preparation of N-(5-benzyloxy-3,4,6-trimethylpyridine-2-yl)pivalamide (7f)

0.161 mL (1.155 mmol) of triethylamine and 0.123 mL (0.990 mmol) of pivaloyl chloride were sequentially added to 10 mL of $CH_2Cl_2$ containing 200 mg (0.825 mmol) of Compound 6, and then, the mixed solution was stirred at room temperature for 10 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 207 mg (77%) of white caramel phase, i.e., Compound 7f.

$^1$H-NMR (250 MHz, $CHCl_3$-d) δ 7.90 (br s, 1H), 7.30-7.45 (m, 5H), 4.74 (s, 2H), 2.40 (s, 3H), 2.22 (s, 3H), 2.04 (s, 3H), 1.32 (s, 9H) ppm

EXAMPLE 7-7

Preparation of N-(5-benzyloxy-3,4,6-trimethylpyridine-2-yl)cyclopentane carboxamide (7g)

0.091 mL (0.654 mmol) of triethylamine and 0.069 mL (0.560 mmol) of cyclopentane carbonyl chloride were sequentially added to 10 mL of $CH_2Cl_2$ containing 113 mg (0.467 mmol) of Compound 6, and then, the mixed solution was stirred at room temperature for 4. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 148 mg (93%) of yellow solids, i.e., Compound 7g.

$^1$H-NMR (250 MHz, $CHCl_3$-d) δ 8.71 (br s, 1H), 7.34-7.45 (m, 5H), 4.74 (s, 2H), 2.73-2.85 (m, 1H), 2.40 (s, 3H), 2.23 (s, 3H), 2.09 (s, 3H), 1.55-1.90 (m, 8H) ppm

EXAMPLE 7-8

Preparation of N-(5-benzyloxy-3,4,6-trimethylpyridine-2-yl)cyclohexane carboxamide (7h)

0.161 mL (1.155 mmol) of triethylamine and 0.132 mL (0.990 mmol) of cyclohexanonyl chloride were sequentially added to 10 mL of $CH_2Cl_2$ containing 200 mg (0.825 mmol) of Compound 6, and then, the mixed solution was stirred at room temperature for 5 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:1), thereby obtaining 103 mg (35%) of white solids, i.e., Compound 7h.

$^1$H-NMR (250 MHz, $CHCl_3$-d) δ 8.00 (br s, 1H), 7.33-7.45 (m, 5H), 4.75 (s, 2H), 2.40 (s, 3H), 2.29-2.35 (m, 1H), 2.23 (s, 3H), 2.08 (s, 3H), 1.94-2.00 (m, 2H), 1.78-1.81 (m, 2H), 1.46-1.61 (m, 2H), 1.19-1.38 (m, 4H) ppm

EXAMPLE 7-9

Preparation of N-(5-benzyloxy-3,4,6-trimethylpyridine-2-yl)-2-penylacetamide (7i)

0.161 mL (1.155 mmol) of triethylamine and 0.134 mL (0.990 mmol) of phenylacetyl chloride were sequentially added to 10 mL of $CH_2Cl_2$ containing 200 mg (0.825 mmol) of Compound 6, and then, the mixed solution was stirred at room temperature for 5 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:1), thereby obtaining 190 mg (64%) of white solids, i.e., Compound 7i $^1$H-NMR (250 MHz, $CHCl_3$-d) δ 8.08 (br s, 1H), 7.26-7.44 (m, 10H), 4.72 (s, 2H), 3.74 (s, 2H), 2.36 (s, 3H), 2.20 (s, 3H), 2.04 (s, 3H) ppm

EXAMPLE 7-10

Preparation of N-(5-benzyloxy-3,4,6-trimethylpyridine-2-yl)-3-phenylpropanamide (7j)

0.161 mL (1.155 mmol) of triethylamine and 0.147 mL (0.990 mmol) of hydrocinnamoyl chloride were sequentially added to 10 mL of $CH_2Cl_2$ containing 200 mg (0.825 mmol) of Compound 6, and the mixed solution was stirred at room temperature for 8 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 310 mg (99%) of white solids, i.e., Compound 7j.

$^1$H-NMR (250 MHz, $CHCl_3$-d) δ 8.33 (br s, 1H), 7.14-7.44 (m, 10H), 4.74 (s, 2H), 3.02 (t, J=7.2 Hz, 2H), 2.70 (t, J=8.2 Hz, 2H), 2.38 (s, 3H), 2.22 (s, 3H), 2.03 (s, 3H) ppm

EXAMPLE 7-11

Preparation of N-(5-benzyloxy-3,4,6-trimethylpyridine-2-yl)benzamide (7k)

0.136 mL (0.965 mmol) of triethylamine and 0.096 mL (0.827 mmol) of benzoyl chloride were sequentially added to 10 mL of $CH_2Cl_2$ containing 167 mg (0.689 mmol) of Compound 6, and the mixed solution was stirred at room temperature for 12 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:5), thereby obtaining 206 mg (86%) of white caramel phase, i.e., Compound 7k.

EXAMPLE 7-12

Preparation of N-(5-benzyloxy-3,4,6-trimethylpyridine-2-yl)-4-fluorobenzamide (7l)

0.161 mL (1.155 mmol) of triethylamine and 0.119 mL (0.990 mmol) of 4-fluorobenzoyl chloride were sequentially added to 10 mL of $CH_2Cl_2$ containing 200 mg (0.825 mmol) of Compound 6, and then, the mixed solution was stirred at room temperature for 5 hours. The reaction solution was diluted with 100 mL of $CH_2Cl_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 218 mg (72%) of white solids, i.e., Compound 7l.

$^1$H-NMR (250 MHz, CHCl$_3$-d) δ 8.86 (br s, 1H), 7.93-7.98 (m, 2H), 7.31-7.46 (m, 5H), 7.06-7.13 (m, 2H), 4.76 (s, 2H), 2.39 (s, 3H), 2.27 (s, 3H), 2.17 (s, 3H) ppm

EXAMPLE 7-13

Preparation of N-(5-benzyloxy-3,4,6-trimethylpyridine-2-yl)-4-methoxybenzamide (7m)

0.161 mL (1.155 mmol) of triethylamine and 0.135 mL (0.990 mmol) of 4-methoxybenzoyl chloride were sequentially added to 10 mL of CH$_2$Cl$_2$ containing 200 mg (0.825 mmol) of Compound 6, and the mixed solution was stirred at room temperature for 4 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:3), thereby obtaining 220 mg (71%) of white solids, i.e., Compound 7m.

$^1$H-NMR (250 MHz, CHCl$_3$-d) δ 8.61 (br s, 1H), 7.91 (dd, J=6.8, 1.9 Hz, 2H), 7.31-7.46 (m, 5H), 6.91 (dd, J=6.9, 1.9 Hz, 2H), 4.75 (s, 2H), 3.83 (s, 3H), 2.40 (s, 3H), 2.26 (s, 3H), 2.16 (s, 3H) ppm

EXAMPLE 7-14

Preparation of N-(5-benzyloxy-3,4,6-trimethylpyridine-2-yl)-4-(tert-butyl)benzamide (7n)

0.161 mL (1.155 mmol) of triethylamine and 0.197 mL (0.990 mmol) of 4-tert-butylbenzoyl chloride were sequentially added to 10 mL of CH$_2$Cl$_2$ containing 200 mg (0.825 mmol) of Compound 6, and then, the mixed solution was stirred at room temperature for 3 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 218 mg (66%) of white solids, i.e., Compound 7n.

$^1$H-NMR (250 MHz, CHCl$_3$-d) δ 8.96 (br s, 1H), 7.89 (dd, J=6.7, 1.7 Hz, 2H), 7.31-7.47 (m, 7H), 4.76 (s, 2H), 2.40 (s, 3H), 2.26 (s, 3H), 2.17 (s, 3H), 1.32 (s, 9H) ppm

EXAMPLE 7-15

Preparation of N-(5-benzyloxy-3,4,6-trimethylpyridine-2-yl)benzo[d][1,3]dioxol-5-carboxamide (7o)

0.161 mL (1.155 mmol) of triethylamine and 186 mg (0.990 mmol) of piperonyloyl chloride were sequentially added to 10 mL of CH$_2$Cl$_2$ containing 200 mg (0.825 mmol) of Compound 6, and then, the mixed solution was stirred at room temperature for 5 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 233 mg (73%) of white solids, i.e., Compound 7o.

$^1$H-NMR (250 MHz, CHCl$_3$-d) δ 8.86 (br s, 1H), 7.31-7.52 (m, 7H), 6.80 (d, J=8.1 Hz, 1H), 6.00 (s, 2H), 4.75 (s, 2H), 2.39 (s, 3H), 2.25 (s, 3H), 2.14 (s, 3H) ppm

EXAMPLE 7-16

Preparation of N-(5-benzyloxy-3,4,6-trimethylpyridine-2-yl)-1-naphthamide (7p)

0.161 mL (1.155 mmol) of triethylamine and 0.153 mL (0.990 mmol) of 1-naphthoyl chloride were sequentially added to 10 mL of CH$_2$Cl$_2$ containing 200 mg (0.825 mmol) of Compound 6, and then, the mixed solution was stirred at room temperature for 2 hours. The reaction solution was diluted with 100 mL of CH2Cl2, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 170 mg (60%) of white solids, i.e., Compound 7p.

$^1$H-NMR (250 MHz, CHCl$_3$-d) δ 8.69 (br s, 1H), 8.49-8.53 (m, 1H), 7.83-7.95 (m, 3H), 7.31-7.58 (m, 8H), 4.76 (s, 2H), 2.35 (s, 3H), 2.28-2.29 (m, 6H) ppm

EXAMPLE 7-17

Preparation of N-(5-benzyloxy-3,4,6-trimethylpyridine-2-yl)thiophene-2-carboxamide (7q)

0.161 mL (1.155 mmol) of triethylamine and 0.109 mL (0.990 mmol) of 2-thiophenecarbonyl chloride were sequentially added to 10 mL of CH$_2$Cl$_2$ containing 200 mg (0.825 mmol) of Compound 6, and then, the mixed solution was stirred at room temperature for 5 hours. The reaction solution was diluted with 100 mL of CH$_2$Cl$_2$, and then, washed with 10 mL of saturated sodium hydrogencarbonate aqueous solution twice and 10 mL of water twice. The CH$_2$Cl$_2$ solution was washed with saturated brine, dried with anhydrous MgSO$_4$, filtered, and then, concentrated under reduced pressure. The residues were purified by column chromatography (EtOAC:Hex=1:5), thereby obtaining 188 mg (64%) of yellow caramel phase, i.e., Compound 7q.

$^1$H-NMR (250 MHz, CHCl$_3$-d) δ 7.74 (dd, J=3.7, 1.0 Hz, 1H), 7.33-7.49 (m, 6H), 7.05 (dd, J=4.9, 3.7 Hz, 1H), 4.76 (s, 2H), 2.40 (s, 3H), 2.25 (s, 3H), 2.18 (s, 3H) ppm

EXAMPLE 7-18

Preparation of N-(5-benzyloxy-3,4,6-trimethylpyridine-2-yl)-2-ethyl butanamide (7r)

0.161 mL (1.155 mmol) of triethylamine and 0.140 mL (0.990 mmol) of 2-ethylbutyryl chloride were sequentially added to 10 mL of CH$_2$Cl$_2$ containing 200 mg (0.825 mmol) of Compound 6, and then, the mixed solution was stirred at room temperature for 3 hours. The reaction solution was diluted with 100 mL of CH$_2$Cl$_2$, and then, washed with 10 mL of saturated sodium hydrogencarbonate aqueous solu-

EXAMPLE 7-19

Preparation of N-(5-benzyloxy-3,4,6-trimethylpyridine-2-yl)-2-phenoxyacetamide (7s)

0.161 mL (1.155 mmol) of triethylamine and 0.140 mL (0.990 mmol) of phenoxyacetyl chloride were sequentially added to 10 mL of $CH_2Cl_2$ containing 200 mg (0.825 mmol) of Compound 6, and then, the mixed solution was stirred at room temperature for 2 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:2), thereby obtaining 263 mg (85%) of white solids, i.e., Compound 7s.

$^1$H-NMR (250 MHz, $CHCl_3$-d) δ 8.53 (br s, 1H), 7.29-7.47 (m, 7H), 6.94-7.05 (m, 3H), 4.76 (s, 2H), 4.64 (s, 2H), 2.44 (s, 3H), 2.25 (s, 3H), 2.12 (s, 3H) ppm

EXAMPLE 7-20

Preparation of N-(5-benzyloxy-3,4,6-trimethylpyridine-2-yl)-2-phenylbutanamide (7t)

0.161 mL (1.155 mmol) of triethylamine and 0.169 mL (0.990 mmol) of 2-phenylbutyryl chloride were sequentially added to 10 mL of $CH_2Cl_2$ containing 200 mg (0.825 mmol) of Compound 6, and then, the mixed solution was stirred at room temperature for 5 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 248 mg (77%) of yellow taffy phase, i.e., Compound 7t.

$^1$H-NMR (250 MHz, $CHCl_3$-d) δ 7.90 (br s, 1H), 7.20-7.45 (m, 10H), 4.72 (s, 2H), 3.45 (t, J=7.4 Hz, 1H), 2.34 (s, 3H), 2.16-2.27 (m, 4H), 1.94 (s, 3H), 1.74-1.89 (m, 1H), 0.88 (t, J=7.3 Hz, 3H) ppm

EXAMPLE 7-21

Preparation of N-(5-benzyloxy-3,4,6-trimethylpyridine-2-yl)-2,4,6-trimethylbenzamide (7u)

0.161 mL (1.155 mmol) of triethylamine and 0.168 mL (0.990 mmol) of 2,4,6-trimethylbenzoyl chloride were sequentially added to 10 mL of $CH_2Cl_2$ containing 200 mg (0.825 mmol) of Compound 6, and then, the mixed solution was stirred at room temperature for 12 hours. The reaction solution was diluted with 100 mL of $CH2Cl2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:4), thereby obtaining 104 mg (33%) of white solids, i.e., Compound 7u.

$^1$H-NMR (250 MHz, $CHCl_3$-d) δ 7.56 (br s, 1H), 7.32-7.48 (m, 5H), 6.85 (s, 2H), 4.76 (s, 2H), 2.41 (s, 9H), 2.27 (s, 9H) ppm

EXAMPLE 7-22

Preparation of 3-benzyloxy-N-(5-benzyloxy-3,4,6-trimethylpyridine-2-yl)benzamide (7v)

0.161 mL (1.155 mmol) of triethylamine and 260 mg (0.990 mmol) of 3-benzyloxybenzoyl chloride were sequentially added to 10 mL of $CH_2Cl_2$ containing 200 mg (0.825 mmol) of Compound 6, and then, the mixed solution was stirred at room temperature for 3 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 276 mg (74%) of white solids, i.e., Compound 7v.

$^1$H-NMR (250 MHz, $CHCl_3$-d) δ 8.46 (br s, 1H), 7.31-7.57 (m, 13H), 7.13 (dd, J=7.8, 2.4 Hz, 1H), 5.08 (s, 2H), 4.75 (s, 2H), 2.42 (s, 3H), 2.27 (s, 3H), 2.17 (s, 3H) ppm

EXAMPLE 7-23

Preparation of N-(5-benzyloxy-3,4,6-trimethylpyridine-2-yl)-3,5,5-trimethylhexanamide (7w)

0.161 mL (1.155 mmol) of triethylamine and 0.192 mL (0.990 mmol) of 3,5,5-trimethylhexanoyl chloride were sequentially added to 10 mL of $CH_2Cl_2$ containing 200 mg (0.825 mmol) of Compound 6, and then, the mixed solution was stirred at room temperature for 3 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:2), thereby obtaining 268 mg (85%) of yellow solids, i.e., Compound 7w.

$^1$H-NMR (250 MHz, $CHCl_3$-d) δ 8.47 (br s, 1H), 7.30-7.46 (m, 5H), 4.74 (s, 2H), 2.35-2.48 (m, 4H), 2.23 (s, 3H), 2.15-2.19 (m, 2H), 2.12 (s, 3H), 1.30 (dd, J=14.0, 3.4 Hz, 1H), 1.12 (dd, J=14.0, 6.2 Hz, 1H), 1.04 (d, J=6.1 Hz, 3H), 0.90 (s, 9H) ppm

EXAMPLE 7-24

Preparation of N-(5-benzyloxy-3,4,6-trimethylpyridine-2-yl)-2-(4-chlorophenyl)acetamide (7x)

0.161 mL (1.155 mmol) of triethylamine and 0.149 mL (0.990 mmol) of 4-chlorophenylacetyl chloride were sequentially added to 10 mL of $CH_2Cl_2$ containing 200 mg (0.825 mmol) of Compound 6, and then, the mixed solution was stirred at room temperature for 2 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:1), thereby obtaining 235 mg (72%) of ivory solids, i.e., Compound 7x.

$^1$H-NMR (250 MHz, $CHCl_3$-d) δ 8.29 (br s, 1H), 7.21-7.44 (m, 9H), 4.74 (s, 2H), 3.68 (s, 2H), 2.36 (s, 3H), 2.21 (s, 3H), 2.04 (s, 3H) ppm

EXAMPLE 7-25

Preparation of N-(5-benzyloxy-3,4,6-trimethylpyridine-2-yl)-2,2-dichloroacetamide (7y)

0.161 mL (1.155 mmol) of triethylamine and 0.097 mL (0.990 mmol) of dichloroacetyl chloride were sequentially added to 10 mL of $CH_2Cl_2$ containing 200 mg (0.825 mmol) of Compound 6, and then, the mixed solution was stirred at room temperature for 4 hours. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 217 mg (74%) of white solids, i.e., Compound 7y.

$^1$H-NMR (250 MHz, $CHCl_3$-d) δ 9.53 (br s, 1H), 7.31-7.44 (m, 5H), 6.10 (br s, 1H), 4.77 (s, 2H), 2.42 (s, 3H), 2.25 (s, 3H), 2.14 (s, 3H) ppm

EXAMPLE 7-26

Preparation of N-(5-benzyloxy-3,4,6-trimethylpyridine-2-yl)cinnamide (7z)

0.161 mL (1.155 mmol) of triethylamine and 142 mg (0.833 mmol) of cinnamoyl chloride were sequentially added to 10 mL of $CH_2Cl_2$ containing 200 mg (0.825 mmol) of Compound 6, and then, the mixed solution was stirred for 30 minutes under ice-cooling. The reaction solution was diluted with 100 mL of $CH_2Cl_2$, and then, washed with 10 mL of saturated sodium hydrogencarbonate aqueous solution twice and 10 mL of water twice. The $CH_2Cl_2$ solution was washed with saturated brine, dried with anhydrous $MgSO_4$, filtered, and then, concentrated under reduced pressure. The residues were purified by column chromatography (EtOAC:Hex=1:3), thereby obtaining 211 mg (69%) of white solids, i.e., Compound 7z.

$^1$H-NMR (250 MHz, $CHCl_3$-d) δ 8.37 (br s, 1H), 7.72 (d, J=16 Hz, 1H), 7.33-7.51 (m, 10H), 6.67 (d, J=16 Hz, 1H), 4.77 (s, 2H), 2.43 (s, 3H), 2.25 (s, 3H), 2.17 (s, 3H) ppm

EXAMPLE 8

Preparation of N-(5-hydroxy-3,4,6-trimethylpyridine-2-yl)amide derivatives (8a-8z)

Figure 2:
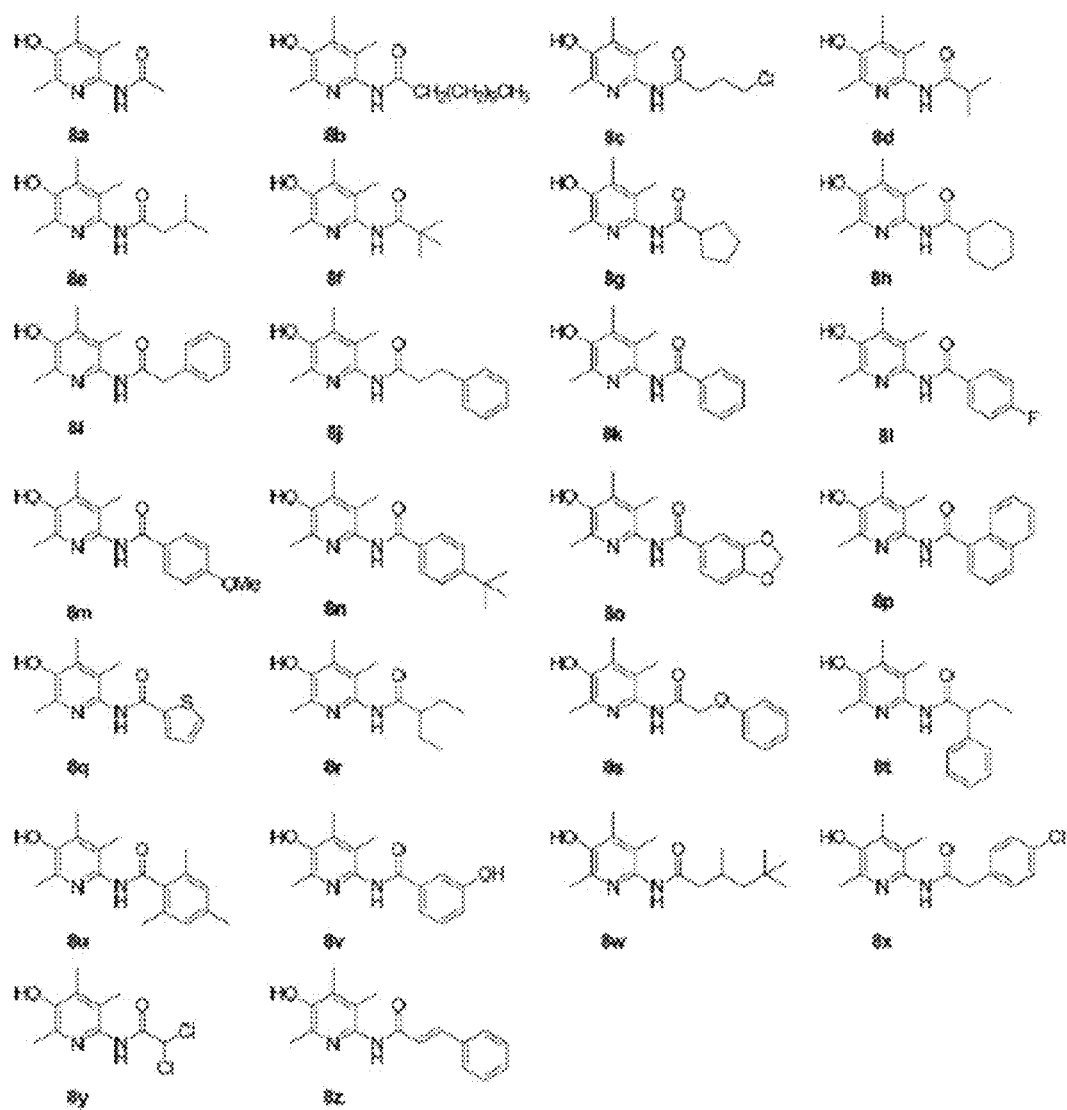
FIG. 2 is a view of amidopyridinol derivatives represented by Chemical Formula 1 according to another exemplary embodiment.
Figure 3:
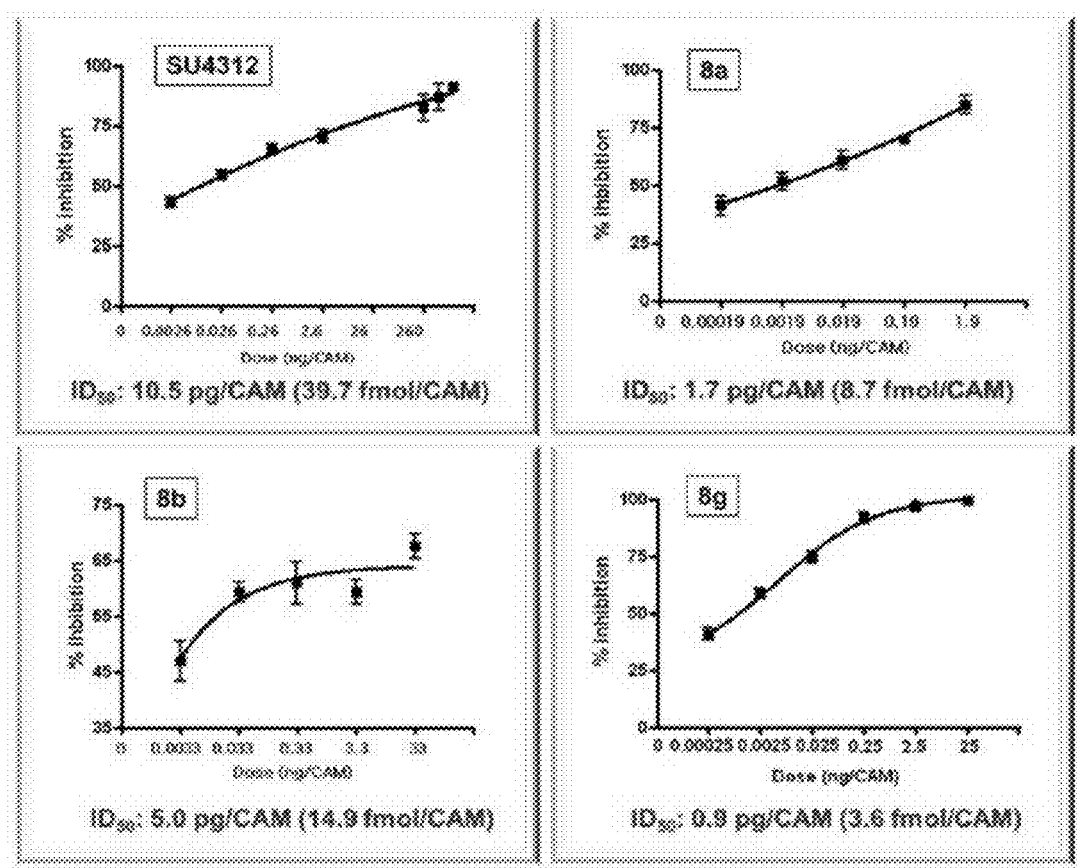
FIG. 3 is shows $ID_{50}$ values against inhibition of angiogenesis of Compounds 8a, 8b, and 8g.

N-(5-hydroxy-3,4,6-trimethylpyridine-2-yl)amide derivatives each prepared in the following manners are shown in FIG. 2.

EXAMPLE 8-1

Preparation of N-(5-hydroxy-3,4,6-trimethylpyridine-2-yl)acetamide (8a)

33 mg of 10% Pd/C was added to 5 mL of methanol containing 164 mg (0.577 mmol) of Compound 7a, and then, the mixed solution was stirred at room temperature for 4 hours under a hydrogen atmosphere. Then, the reaction solution was filtered and concentrated under pressure. The residues were dissolved in methanol, filtered using a syringe filter (Advantec™ JP050AN), and then, concentrated, thereby obtaining 105 mg (94%) of pale yellow solids, i.e., Compound 8a.

$^1$H-NMR (250 MHz, $CH_3OH$-$d_4$) δ 2.30 (s, 3H), 2.15 (s, 3H), 2.08 (s, 3H), 2.05 (s, 3H) ppm

EXAMPLE 8-2

Preparation of N-(5-hydroxy-3,4,6-trimethylpyridine-2-yl)dodecanamide (8b)

25 mg of 10% Pd/C was added to 5 mL of methanol containing 130 mg (0.306 mmol) of Compound 7b, and then, the mixed solution was stirred at room temperature for 10 hours under a hydrogen atmosphere. Then, the reaction solution was filtered, and the filtrate was concentrated under pressure. The residues were dissolved in methanol, filtered using a syringe filter (Advantec™ JP050AN), and then, concentrated, thereby obtaining 77 mg (75%) of pale yellow solids, i.e., Compound 8b.

$^1$H-NMR (250 MHz, DMSO-$d_6$) δ 9.60 (s, 1H), 2.28 (s, 3H), 2.15-2.26 (m, 2H), 2.11 (s, 3H), 1.94 (s, 3H), 1.44-1.54 (m, 2H), 1.23 (s, 16H), 0.85 (t, J=5.5 Hz, 3H) ppm

EXAMPLE 8-3

Preparation of N-(5-hydroxy-3,4,6-trimethylpyridine-2-yl)-4-chlorobutaneamide (8c)

21 mg of 10% Pd/C was added to 5 mL of methanol containing 102 mg (0.294 mmol) of Compound 7c, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 75 mg (99%) of yellow solids, i.e., Compound 8c.

$^1$H-NMR (250 MHz, $CH_3OH$-$d_4$) δ 3.64 (t, J=6.3 Hz, 2H), 2.55 (t, J=7.2 Hz, 2H), 2.33 (s, 3H), 2.18 (s, 3H), 2.12 (t, J=7.0 Hz, 2H), 2.07 (s, 3H) ppm

EXAMPLE 8-4

Preparation of N-(5-hydroxy-3,4,6-trimethylpyridine-2-yl)isobutyryl amide (8d)

31 mg of 10% Pd/C was added to 5 mL of methanol containing 155 mg (0.496 mmol) of Compound 7d, and then, the mixed solution was stirred at room temperature for 3 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 95 mg (86%) of white solids, i.e., Compound 8d.

¹H-NMR (250 MHz, CH₃OH-d₄) δ 2.55-2.72 (m, 1H), 2.33 (s, 3H), 2.18 (s, 3H), 2.05 (s, 3H), 1.22 (s, 3H), 1.19 (s, 3H) ppm

EXAMPLE 8-5

Preparation of N-(5-hydroxy-3,4,6-trimethylpyridine-2-yl)-3-methylbutanamide (8e)

34 mg of 10% Pd/C was added to 5 mL of methanol containing 170 mg (0.520 mmol) of Compound 7e, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 102 mg (82%) of white solids, i.e., Compound 8e.

¹H-NMR (250 MHz, CH₃OH-d₄) δ 2.33 (s, 3H), 2.20-2.25 (m, 2H), 2.18 (s, 3H), 2.12-2.15 (m, 1H), 2.07 (s, 3H), 1.02 (s, 3H), 1.00 (s, 3H) ppm

EXAMPLE 8-6

Preparation of N-(5-hydroxy-3,4,6-trimethylpyridine-2-yl)pivalamide (8f)

32 mg of 10% Pd/C was added to 5 mL of methanol containing 160 mg (0.490 mmol) of Compound 7f, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 80 mg (69%) of white solids, i.e., Compound 8f.

¹H-NMR (250 MHz, CH₃OH-d₄) δ 2.38 (s, 3H), 2.23 (s, 3H), 2.08 (s, 3H), 1.30 (s, 9H) ppm

EXAMPLE 8-7

Preparation of N-(5-hydroxy-3,4,6-trimethylpyridine-2-yl)cyclopentane carboxamide (8g)

20 mg of 10% Pd/C was added to 5 mL of methanol containing 108 mg (0.319 mmol) of Compound 7g, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 66 mg (83%) of white solids, i.e., Compound 8g.

¹H-NMR (250 MHz, CH₃OH-d₄) δ 2.77-2.86 (m, 1H), 2.33 (s, 3H), 2.19 (s, 3H), 2.06 (s, 3H), 1.61-1.96 (m, 8H) ppm

EXAMPLE 8-8

Preparation of N-(5-hydroxy-3,4,6-trimethylpyridine-2-yl)cyclohexane carboxamide (8h)

15 mg of 10% Pd/C was added to 10 mL of methanol-THF solution containing 73 mg (0.207 mmol) of Compound 7h, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 54 mg (99%) of white solids, i.e., Compound 8h.

¹H-NMR (250 MHz, DMSO-d₆) δ 9.43 (s, 1H), 2.28 (s, 3H), 2.11 (s, 3H), 1.92 (s, 3H), 1.62-1.81 (m, 4H), 1.13-1.46 (m, 6H) ppm

EXAMPLE 8-9

Preparation of N-(5-hydroxy-3,4,6-trimethylpyridine-2-yl)-2-penylacetamide (8i)

28 mg of 10% Pd/C was added to 5 mL of methanol containing 141 mg (0.393 mmol) of Compound 7i, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 37 mg (35%) of white solids, i.e., Compound 8i.

¹H-NMR (250 MHz, CH₃OH-d₄) δ 7.16-7.36 (m, 5H), 3.63 (s, 2H), 2.29 (s, 3H), 2.11 (s, 3H), 1.91 (s, 3H) ppm

EXAMPLE 8-10

Preparation of N-(5-hydroxy-3,4,6-trimethylpyridine-2-yl)-3-phenylpropanamide (8j)

58 mg of 10% Pd/C was added to 10 mL of methanol containing 291 mg (0.779 mmol) of Compound 7j, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 186 mg (84%) of white solids, i.e., Compound 8j.

¹H-NMR (250 MHz, CH₃OH-d₄) δ 7.11-7.25 (m, 5H), 2.98 (t, J=7.3 Hz, 2H), 2.68 (t, J=7.9 Hz, 2H), 2.33 (s, 3H), 2.15 (s, 3H), 1.89 (s, 3H) ppm

EXAMPLE 8-11

Preparation of N-(5-hydroxy-3,4,6-trimethylpyridine-2-yl)benzamide (8k)

37 mg of 10% Pd/C was added to 10 mL of methanol containing 186 mg (0.539 mmol) of Compound 7k, and then, the mixed solution was stirred at room temperature for 4 hours under a hydrogen atmosphere. The reaction solution was filtered, and the filtrate was concentrated under pressure. The residues were purified by column chromatography (EtOAc:Hex=1:1), and then, concentrated under pressure. The residues were again dissolved in methanol, and then, the mixed solution was filtered using a syringe filter (Advantec™ JP050AN), and then, concentrated, thereby obtaining 86 mg (62%) of white solids, i.e., Compound 8k.

¹H-NMR (250 MHz, CH₃OH-d₄) δ 7.93-7.97 (m, 2H), 7.44-7.59 (m, 3H), 2.36 (s, 3H), 2.21 (s, 3H), 2.13 (s, 3H) ppm

EXAMPLE 8-12

Preparation of N-(5-hydroxy-3,4,6-trimethylpyridine-2-yl)-4-fluorobenzamide (8l)

38 mg of 10% Pd/C was added to 10 mL of methanol containing 180 mg (0.493 mmol) of Compound 7l, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 135 mg (99%) of white solids, i.e., Compound 81.

$^1$H-NMR (250 MHz, CH$_3$OH-d$_4$) δ 7.99-8.05 (m, 2H), 7.18-7.25 (m, 2H), 2.37 (s, 3H), 2.22 (s, 3H), 2.13 (s, 3H) ppm

EXAMPLE 8-13

Preparation of N-(5-hydroxy-3,4,6-trimethylpyridine-2-yl)-4-methoxybenzamide (8m)

40 mg of 10% Pd/C was added to 10 mL of methanol containing 200 mg (0.531 mmol) of Compound 7m, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 151 mg (99%) of white solids, i.e., Compound 8m.

$^1$H-NMR (250 MHz, CH$_3$OH-d$_4$) δ 7.93-7.96 (m, 2H), 6.99-7.03 (m, 2H), 3.85 (s, 3H), 2.37 (s, 3H), 2.23 (s, 3H), 2.13 (s, 3H) ppm

EXAMPLE 8-14

Preparation of N-(5-hydroxy-3,4,6-trimethylpyridine-2-yl)-4-(tert-butyl)benzamide (8n)

40 mg of 10% Pd/C was added to 10 mL of methanol containing 205 mg (0.509 mmol) of Compound 7n, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 157 mg (99%) of white solids, i.e., Compound 8n.

$^1$H-NMR (250 MHz, DMSO-d$_6$) δ 7.94 (d, J=8.3 Hz, 2H), 7.52 (d, J=8.4 Hz, 2H), 2.37 (s, 3H), 2.19 (s, 3H), 2.03 (s, 3H), 1.31 (s, 9H) ppm

EXAMPLE 8-15

Preparation of N-(5-hydroxy-3,4,6-trimethylpyridine-2-yl)benzo[d][1,3]dioxol-5-carboxamide (8o)

44 mg of 10% Pd/C was added to 10 mL of methanol containing 222 mg (0.568 mmol) of Compound 7o, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 170 mg (99%) of white solids, i.e., Compound 8o.

$^1$H-NMR (250 MHz, CH$_3$OH-d$_4$) δ 7.55 (dd, J=8.1, 1.8 Hz, 1H), 7.40 (d, J=1.2 Hz 1H), 6.89 (d, J=8.1 Hz, 1H), 6.03 (s, 2H), 2.36 (s, 3H), 2.23 (s, 3H), 2.12 (s, 3H) ppm

EXAMPLE 8-16

Preparation of N-(5-hydroxy-3,4,6-trimethylpyridine-2-yl)-1-naphthamide (8p)

22 mg of 10% Pd/C was added to 5 mL of methanol containing 110 mg (0.277 mmol) of Compound 7p, and then, the mixed solution was stirred at room temperature for 10 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 104 mg (99%) of white solids, i.e., Compound 8p.

$^1$H-NMR (250 MHz, CH$_3$OH-d$_4$) δ 8.31-8.35 (m, 1H), 7.95-7.96 (m, 1H), 7.86-7.89 (m, 2H), 7.47-7.53 (m, 3H), 2.42 (s, 3H), 2.25 (s, 3H), 2.23 (s, 3H) ppm

EXAMPLE 8-17

Preparation of N-(5-hydroxy-3,4,6-trimethylpyridine-2-yl)thiophene-2-carboxamide (8q)

0.91 mL (0.91 mmol) of 1 M BCl$_3$ was added dropwise to 10 mL of CH$_2$Cl$_2$ containing 160 mg (0.454 mmol) of Compound 7q and 201 mg (1.362 mmol) of pentamethylbenzene, and then, the mixed solution was stirred for another 30 minutes under ice-cooling. 1 mL of CHCl$_3$/MeOH (9:1) was added to the reaction solution, and then, the mixed solution was stirred at room temperature for 1 hour. The reaction solution was concentrated under pressure, and then, the residues were purified by column chromatography (CHCl$_3$:MeOH=9:1), thereby obtaining 115 mg (96%) of yellow solids, i.e., Compound 8q.

$^1$H-NMR (250 MHz, DMSO-d$_6$) δ 10.2 (s, 1H), 8.56 (s, 1H), 7.98 (d, J=3.1 Hz, 1H), 7.80 (d, J=4.5 Hz, 1H), 7.17-7.21 (m, 1H), 2.33 (s, 3H), 2.16 (s, 3H), 2.02 (s, 3H) ppm

EXAMPLE 8-18

Preparation of 2-ethyl-N-(5-hydroxy-3,4,6-trimethylpyridine-2-yl)butanamide (8r)

30 mg of 10% Pd/C was added to 10 mL of methanol containing 150 mg (0.441 mmol) of Compound 7r, and then, the mixed solution was stirred at room temperature for 5 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 110 mg (99%) of white solids, i.e., Compound 8r.

$^1$H-NMR (250 MHz, DMSO-d$_6$) δ 9.55 (s, 1H), 2.29 (s, 3H), 2.16-2.25 (m, 1H), 2.12 (s, 3H), 1.97 (s, 3H), 1.33-1.64 (m, 4H), 0.90 (t, J=7.4 Hz, 6H) ppm

EXAMPLE 8-19

Preparation of N-(4-hydroxy-3,4,6-trimethylpyridine-2-yl)-2-phenoxyacetamide (8s)

30 mg of 10% Pd/C was added to 10 mL of methanol containing 150 mg (0.398 mmol) of Compound 7s, and then, the mixed solution was stirred at room temperature for 5 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 120 mg (99%) of white solids, i.e., Compound 8s.

$^1$H-NMR (250 MHz, DMSO-$d_6$) δ 9.79 (s, 1H), 7.27-7.35 (m, 2H), 6.94-7.02 (m, 3H), 4.66 (s, 2H), 2.30 (s, 3H), 2.13 (s, 3H), 1.97 (s, 3H) ppm

EXAMPLE 8-20

Preparation of N-(5-hydroxy-3,4,6-trimethylpyridine-2-yl)-2-phenyl butanamide (8t)

35 mg of 10% Pd/C was added to 10 mL of methanol containing 176 mg (0.453 mmol) of Compound 7t, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 135 mg (99%) of yellow solids, i.e., Compound 8t.

$^1$H-NMR (250 MHz, DMSO-$d_6$) δ 9.81 (s, 3H), 8.44 (s, 1H), 7.19-7.40 (m, 5H), 3.57 (dd, J=8.6, 6.5 Hz, 1H), 2.26 (s, 3H), 2.09 (s, 3H), 1.97-2.06 (m, 1H), 1.80 (s, 3H), 1.61-1.72 (m, 1H), 0.88 (t, J=7.3 Hz, 3H) ppm

EXAMPLE 8-21

Preparation of N-(5-hydroxy-3,4,6-trimethylpyridine-2-yl)-2,4,6-trimethylbenzamide (8u)

19 mg of 10% Pd/C was added to 10 mL of methanol containing 94 mg (0.242 mmol) of Compound 7u, and then, the mixed solution was stirred at room temperature for 7 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 72 mg (99%) of white solids, i.e., Compound 8u.

$^1$H-NMR (250 MHz, DMSO-$d_6$) δ 9.82 (s, 1H), 6.88 (s, 2H), 2.33 (s, 9H), 2.25 (s, 3H), 2.16 (s, 3H), 2.15 (s, 3H) ppm

EXAMPLE 8-22

Preparation of 3-hydroxy-N-(5-hydroxy-3,4,6-trimethylpyridine-2-yl)benzamide (8v)

30 mg of 10% Pd/C was added to 10 mL of methanol containing 150 mg (0.33 mmol) of Compound 7v, and then, the mixed solution was stirred at room temperature for 3 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 42 mg (47%) of white solids, i.e., Compound 8v.

$^1$H-NMR (250 MHz, DMSO-$d_6$) δ 10.02 (s, 1H), 7.24-7.43 (m, 3H), 6.95 (dd, J=7.6, 2.1 Hz, 1H), 2.32 (s, 3H), 2.16 (s, 3H), 2.00 (s, 3H) ppm

EXAMPLE 8-23

Preparation of N-(5-hydroxy-3,4,6-trimethylpyridine-2-yl)-3,5,5-trimethylhexanamide (8w)

37 mg of 10% Pd/C was added to 12 mL of methanol containing 186 mg (0.48 mmol) of Compound 7w, and then, the mixed solution was stirred at room temperature for 4 hours under a hydrogen atmosphere. The reaction solution was filtered, and the filtrate was concentrated under pressure. The residues were dissolved in methanol, filtered using a syringe filter (Advantec™ JP050AN), and then, concentrated, thereby obtaining 130 mg (93%) of yellow solids, i.e., Compound 8w.

$^1$H-NMR (250 MHz, DMSO-$d_6$) δ 9.52 (s, 1H), 2.28 (s, 3H), 2.18-2.25 (m, 1H), 2.11 (s, 3H), 2.04-2.09 (m, 2H), 1.96 (s, 3H), 1.31 (dd, J=13.8, 3.0 Hz, 1H), 1.07 (dd, J=13.9, 6.2 Hz, 1H), 0.97 (d, J=6.1 Hz, 3H), 0.89 (s, 9H) ppm

EXAMPLE 8-24

Preparation of 2-(4-chlorophenyl)-N-(5-hydroxy-3,4,6-trimethylpyridine-2-yl)acetamide (8x)

0.66 mL (0.66 mmol) of 1 M $BCl_3$ was added dropwise to 5 mL of $CH_2Cl_2$ containing 130 mg (0.329 mmol) of Compound 7x and 146 mg (0.987 mmol) of pentamethylbenzene, and then, the mixed solution was stirred for 2 hours under ice-cooling. 1 mL of $CHCl_3$/MeOH (9:1) was added to the reaction solution, and then, the mixed solution was stirred at room temperature for 1 hour. The reaction solution was concentrated under pressure, and then, the residues were purified by column chromatography ($CHCl_3$:MeOH=9:1), thereby obtaining 94 mg (94%) of white solids, i.e., Compound 8x.

$^1$H-NMR (250 MHz, DMSO-$d_6$) δ 9.85 (br s, 1H), 8.46 (s, 1H), 7.32-7.40 (m, 4H), 3.59 (s, 2H), 2.29 (s, 3H), 2.10 (s, 3H), 1.87 (s, 3H) ppm

EXAMPLE 8-25

Preparation of 2,2-dichloro-N-(5-hydroxy-3,4,6-trimethylpyridine-2-yl)acetamide (8y)

0.91 mL (0.91 mmol) of 1 M $BCl_3$ was added dropwise to 7 mL of $CH_2Cl_2$ containing 161 mg (0.456 mmol) of Compound 7y and 203 mg (1.367 mmol) of pentamethylbenzene, and then, the mixed solution was stirred for 1 hour under ice-cooling. 1 mL of $CHCl_3$/MeOH (9:1) was added to the reaction solution, and then, the mixed solution was stirred at room temperature for 1 hour. The reaction solution was concentrated under pressure, and then, the residues were purified by column chromatography ($CHCl_3$:MeOH=9:1), thereby obtaining 110 mg (92%) of white solids, i.e., Compound 8y.

$^1$H-NMR (250 MHz, DMSO-$d_6$) δ 10.34 (br s, 1H), 8.64 (br s, 1H), 6.60 (s, 1H), 2.31 (s, 3H), 2.14 (s, 3H), 1.98 (s, 3H) ppm

EXAMPLE 8-26

Preparation of N-(5-hydroxy-3,4,6-trimethylpyridine-2-yl)cinnamide (8z)

0.75 mL (0.75 mmol) of 1 M $BCl_3$ was added dropwise to 7 mL of $CH_2Cl_2$ containing 140 mg (0.376 mmol) of Compound 7z and 167 mg (1.127 mmol) of pentamethylbenzene, and then, the mixed solution was stirred for 2 hours under ice-cooling. 1 mL of $CHCl_3$/MeOH (9:1) was added to the reaction solution, and then, the mixed solution was stirred at room temperature for 1 hour. The reaction solution was concentrated under pressure, and then, the residues were purified by column chromatography (CHCl$_3$:MeOH=9:1), thereby obtaining 45 mg (42%) of yellow solids, i.e., Compound 8z.

$^1$H-NMR (250 MHz, DMSO-d$_6$) δ 10.34 (br s, 1H), 8.64 (br s, 1H), 6.60 (s, 1H), 2.31 (s, 3H), 2.14 (s, 3H), 1.98 (s, 3H) ppm Experimental Example 1

Review of Inhibitory Effects on Angiogenesis by CAM Analysis

To confirm inhibitory effects on angiogenesis through in vivo experiments, the chorioallantoic membrane (CAM) analysis was carried out (refer to Nguyen M et al., Microvascular Res., 47, pp 31-40, 1994). A fertilized egg of a chicken was cultured in conditions maintaining a temperature of 37° C. and relative humidity of 55%. On the 10$^{th}$ day of the culturing, a first small hole was made on an air sac part using a hypodermic needle (Green Cross Medical Corp., Korea), and then, a second hole was made on a flat part of the fertilized egg to make a window thereon. Air was removed through the first hole, i.e., the air sac part, and accordingly, the CAM was separated from the shell of the fertilized egg. Then, a grinding wheel (Multipro 395JA, Dremel, Mexico) was used to cut the air sac part, thereby making a window thereon. Next, the whatman filter disk #1 (Whatman Company, USA) was treated with 3 mg/mL of cortisone acetate, dried, and then, wet by VEGF at a concentration of 20 ng/CAM. The filter disk was placed on blood vessels through the window, and then, compounds prepared according to Examples above were each dissolved in DMSO, diluted with PBS, and then, treated for each concentration. After 3 days of treating the compounds, the CAM part on which the filter disk was placed was isolated, and then, washed with PBS. The Stemi SV6 stereomicroscope (Carl Zeiss, Germany) and the Image-Pro Plus software (Media Cybernetics; Silver Spring, Md., USA) were used to capture images of the CAM part, so as to measure the number of the blood vessels and to analyze data obtained therefrom.

Consequently, as shown in Table 1 below, it was confirmed that the increase angiogenesis upon the VEGF was decreased by the treatment with the compounds of the present invention (treatment of 0.01 mnol of each compound per CAM). In addition, excellent angiogenesis inhibitory effects were observed in most cases. In addition, as a result of calculating ID$_{50}$ after treating CAM with Compounds 8a, 8b, and 8g at each concentration, as shown in Table 3, the results are as follows: 1.7 pg/CAM (8.7 fmol/CAM), 5.0 pg/CAM (14.9 fmol/CAM), and 0.9 pg/CAM (3.6 fmol/CAM).

TABLE 1

| Experimental groups | | Inhibitory rates (%) |
|---|---|---|
| VEGF (20 ng/CAM) + Compound (0.01 nmol/CAM) | SU4312 | 74.6 ± 8.5# |
| | 8a | 84.8 ± 10.0# |
| | 8b | 59.3 ± 5.4# |
| | 8c | 70.2 ± 4.6# |
| | 8d | 53.2 ± 11.5# |
| | 8e | 75.6 ± 8.9# |
| | 8f | 73.2 ± 6.4# |
| | 8g | 81.8 ± 8.4# |
| | 8h | 76.3 ± 7.2# |

TABLE 1-continued

| Experimental groups | Inhibitory rates (%) |
|---|---|
| 8i | 69.6 ± 11.0# |
| 8j | 74.2 ± 3.9# |
| 8k | 77.3 ± 13.1# |
| 8l | 75.3 ± 6.3# |
| 8m | 69.7 ± 4.5# |
| 8n | 74.2 ± 7.0# |
| 8o | 64.8 ± 17.4# |
| 8p | 75.8 ± 5.4# |
| 8q | 74.8 ± 13.2# |

P < 0.05 compared to VEGF-treated group.

Experimental Example 2

Measurement of Scavenging Effects of Reactive Oxygen Species (ROS) in HUVEC Cells To measure scavenging effects of ROS in HUVEC cells that were induced by VEGF, 2',7'-dichlorofluorescein diacetate (DCF-DA) was used. In the presence of ROS in the cells DCF-DA is oxidized to fluorescent DCF, and accordingly, exhibits green fluorescence. After DCF-DA was divided into the 8-well plates at a concentration of 1×10$^5$, each of which well was coated with 0.2% gelatin, DCF-DA was cultured for 24 hours. Meanwhile, Compounds 8a and 8b were pre-treated for 3 hours, induced by VEGF for 15 minutes, and then, washed with PBS (pH 7.4) three times. Then, 10 µM of DCF-DA was placed in a EBM-2 medium to be treated for 30 minutes in a dark room. Then, DCF-DA was washed again with PBS three times, and then, subjected to measure intensity of fluorescence in the cells by using a fluorescence microscope.

Figure 4:
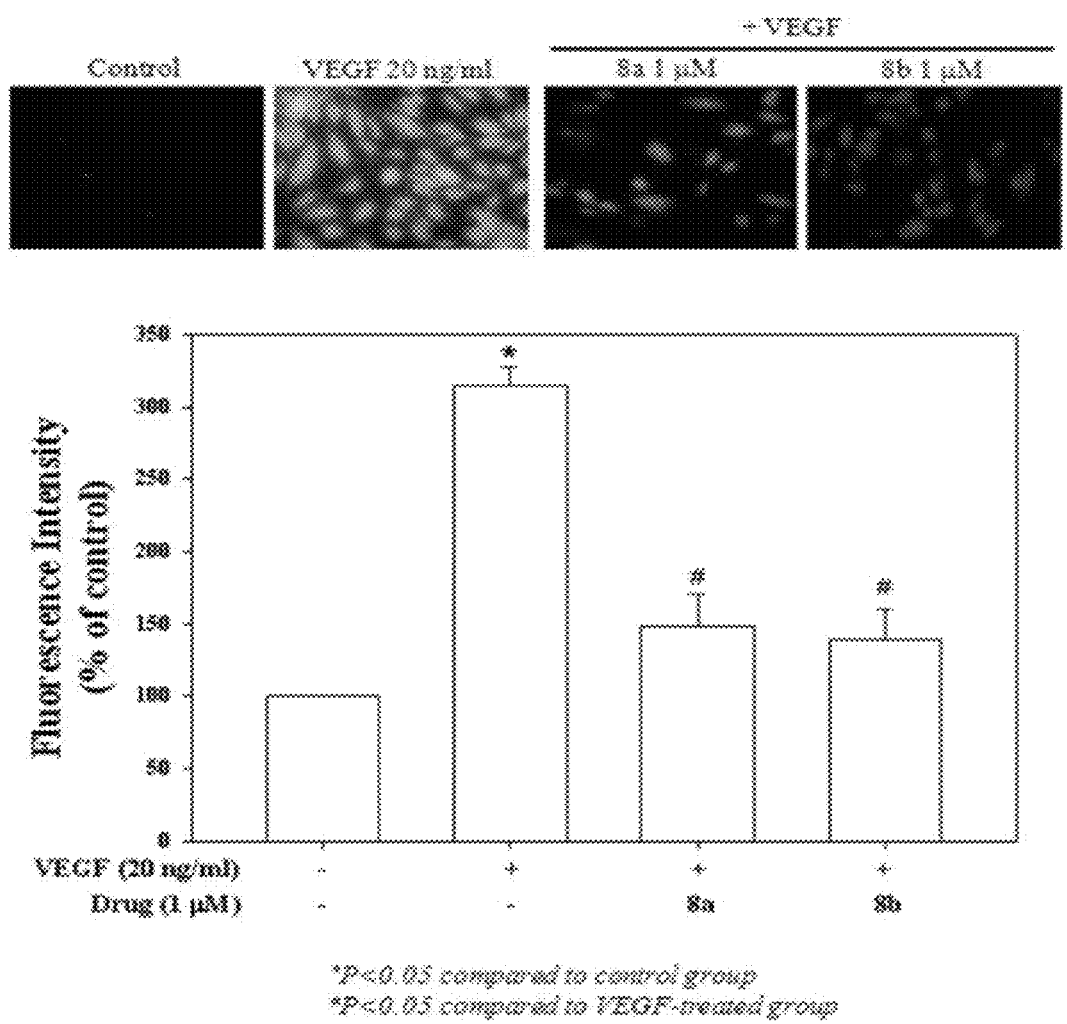
FIG. 4 shows results of vascular endothelial growth factor (VEGF)-induced ROS scavenging activities of Compounds 8a and 8b.

Consequently, as shown in FIG. 4, a case where Compounds 8a and 8b were treated showed a significant decrease in the intensity of fluorescence in the cells, compared to a case where the cells were induced by VEGF.

Experimental Example 3

Measurement of Scavenging Effects of ROS Induced by Risk Factors of Macular Degeneration According to a similar manner as in Experimental Example 2, a risk factor of macular degeneration, e.g., 4-hydroxynonenal (4-HNE) or angiotensin II (Ang II), were treated with an adult retinal pigment epithelium-19 (ARPE-19) cell line, so as to observe scavenging effects of ROS in Compounds 8a and 8b.

Figure 5:
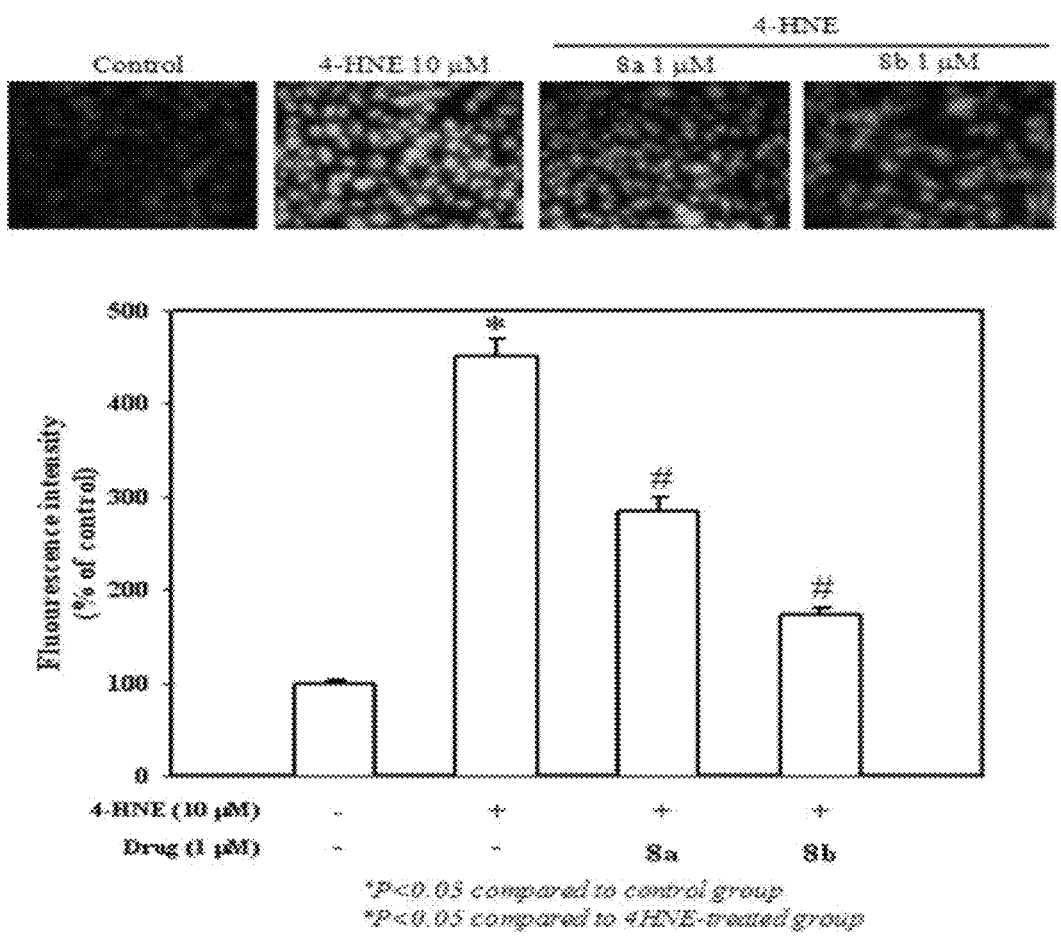
FIG. 5 shows results of VEGF-induced ROS scavenging activities of Compounds 8a and 8b by treating ARPE-19 cell lines with 4-hydroxynonenal (4-HNE), which is a risk factor of macular degeneration.
Figure 6:
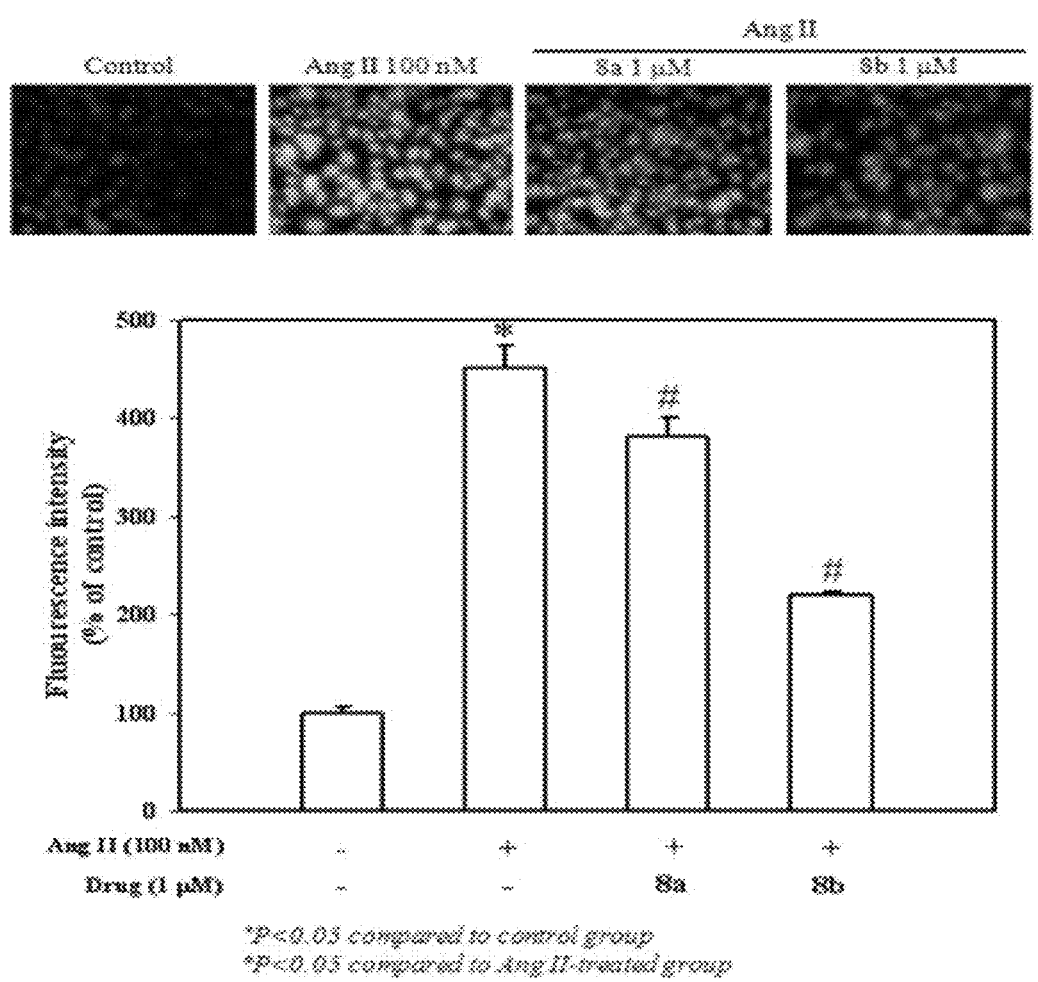
FIG. 6 shows results of VEGF-induced ROS scavenging activities of Compounds 8a and 8b by treating ARPE-19 cell lines with angiotensin II (Ang II), which is a risk factor of macular degeneration.

Consequently, as shown in FIGS. 5A and 6, it was confirmed that a case where Compounds 8a and 8b were treated showed a significant decrease in the intensity of fluorescence, compared to the control group.

The risk factor of macular degeneration, e.g., 4-HNE or Ang II, causes cell damages in the ARPE cells due to the occurrence of ROS, and eventually, may cause damages in Bruch's membrane and angiogenesis, resulting in macular degeneration and blindness. Based on the experimental data, it was confirmed that Compounds 8a and 8b strongly inhibited the occurrence of ROS upon 4-HNE and Ang II, and that is, Compounds 8a and 8b had therapeutic effects on macular degeneration.

Experimental Example 4

Inhibitory Effects on Adhesion of Intestinal Epithelial Cells-Mononuclear of Amidopyridinol Derivative in HT-29 Intestinal Epithelial Cells HT-29 cells were cultured in a 24-well plate at a concentration of 2×10 cells/cm$^2$, and meanwhile, amidopyridinol compounds 8a to 8z were pre-treated for 1 hour at each concentration in a serum-free medium supplemented only with 1% PS. Next, 10 ng/ml of TNF-α was treated therewith to allow a reaction at a temperature of 37° C. for 3 hours. After the completion of the reaction, the medium of the HT-29 cells was removed, and then, the HT-29 cells were washed with PBS once. Afterwards, U937 cells, which were treated and reacted with 10 μg/mL of BCECF-AM at a temperature of 37° C. for 30 minutes, were allowed to react with the HT-29 cells at temperature of 37° C. for 1 hour. Then, to remove U937 cells that were not adhered to the HT-29 cells, the reacted cells were washed with PBS twice. In terms of cell dissolution, 0.1% Triton X-100 in 0.1M Tris was allowed to react with the cells for 30 minutes at room temperature, and then, the cells were subjected to quantify by measuring fluorescence thereof using the Fluostar optima microplate reader (BMG Labtechnologies, Germany).

Consequently, in Table 2 below, the inhibitory effects of amidopyridinol compounds 8a to 8z on adhesion with the human-derived intestinal epithelial cells (i.e., HT-29) induced by TNF-α and the mononuclear cells (i.e., U937) are shown. Here, * indicates a case where a P value is smaller than 0.05 compared to a case where the rat was treated with TNF-α. As shown in Table 2, it was confirmed that amidopyridinol compounds 8a to 8z inhibited the adhesion between the intestinal epithelial cells induced by TNF-α and the U937 cells.

TABLE 2

| Experimental groups | Inhibitory rates (%) |
|---|---|
| 5-ASA (20 mM) | 46.8* |
| 8a (1 μM) | 55.4* |
| 8b (1 μM) | 55.8* |
| 8c (1 μM) | 24.7 |
| 8d (1 μM) | 52.3* |
| 8e (1 μM) | 64.2* |
| 8f (1 μM) | 37.5 |
| 8g (1 μM) | 42.8* |
| 8h (1 μM) | 64.5* |
| 8i (1 μM) | 56.6* |
| 8j (1 μM) | 72.5* |
| 8k (1 μM) | 18.5 |
| 8l (1 μM) | 13.7 |
| 8m (1 μM) | 13.9 |
| 8n (1 μM) | 22.5 |
| 8o (1 μM) | 40.2 |
| 8p (1 μM) | 64.9* |
| 8q (1 μM) | 68.4* |
| 8r (1 μM) | 4.2 |
| 8s (1 μM) | 10.8 |
| 8t (1 μM) | 23.6* |
| 8u (1 μM) | 30.4 |
| 8v (1 μM) | 54.1* |
| 8w (1 μM) | 54.5* |
| 8x (1 μM) | 41.5* |
| 8y (1 μM) | 60.6* |
| 8z (1 μM) | 25.2 |

Based on the results above, it was determined that, when amidopyridinol derivatives 8a to 8z inhibit the adhesion of inflammatory cells, e.g., neutrophils and lymphocytes, that are closely related to the movement of inflammatory cells and the invasion of cancer, the inflammatory responses can be also inhibited.

Experimental Example 5

Colitis-Inhibitory Effects of Amidopyridinol Derivatives Using a Model of Inflammatory Bowel Diseases Induced by 2,4,6-Trinitrobenzenesulfonic Acid (TNBS)

To see alleviating effects of the compounds of the present invention on colitis, an animal model induced by TNBS and having colitis was used for the experiments. The animal used herein was a 7 to 8 week Sprague Dawley species purchased from Samtaco Bio Korea. After the purchase, the animal was stabilized with typical solid feed for 2 days before being used for the experiments. The animal was freely supplied with feed and water during the experiments, and stayed in conditions maintaining a cage temperature of about 25±1° C. and relative humidity of about 50±10%. The cage was equipped with an automatic lightening system to adjust 12-hour light-dark cycle.

In regard to the experimental groups, 5 groups (i.e., a control group, a group administered with TNBS only, a group administered in combination of TNBS+5-ASA 300 mg/kg, a group administered in combination of TNBS+8a and 8j 0.1 mg/kg, and a group administered in combination of TNBS+8a and 8j 1.0 mg/kg) were used according to the randomized block design, wherein each group consists of 6 rats having an average weight of about 180±10 g. The rats that had been fasting for 24 hours were anesthetized with diethylether (Et$_2$O), and then, a 1 mL syringe connected with a polyethylene catheter was used to slowly inject 0.8 mL of 3% TNBS into colonic enema through the anus, wherein TNBS was diluted with 50% (v/v) ethanol. To prevent leakage of 3% TNBS from the anus, the rats turned upside down and let stand for 60 minutes.

In regard to the control group, only a vehicle (50% (v/v) ethanol) was injected into the rats of the control group in the same manner as in preparation of other experimental groups. To examine the effects of the drug, after being fasting for 24 hours, the rats were administered with drugs, i.e., 0.1 mg/kg or 1.0 mg/kg of Compounds 8a and 8j, once a day at a certain time from the second day to the fifth day of the TNBS treatment. As a comparative experimental material, 5-ASA, which is an active metabolite of sulfasalazine that is the most well-known as a therapeutic agent for IBDs, was used as a positive control group.

All the rats were scarified on the seventh day of the TNBS administration. The visible severity of ulcer and colitis was evaluated by two investigators who did not participate in the experiments. After the large intestine of the rat was harvested, a 5 to 6 cm-long tissue from was cut from the anus to a size of 1 cm, and then, subjected to measure an intestine weight and activation of myeloperoxidase (MPO) in the tissue, and to perform a biopsy. In addition, changes in weight of all the animals used in the experiments were observed by using a digital mass meter, beginning from the fasting step, the TNBS administration, and the drug administration. In consideration of the management and use of laboratory animals, the animal experiments were followed according to institutional guidelines from Laboratory Animal Resources, Yeungnam University.

Figure 7:
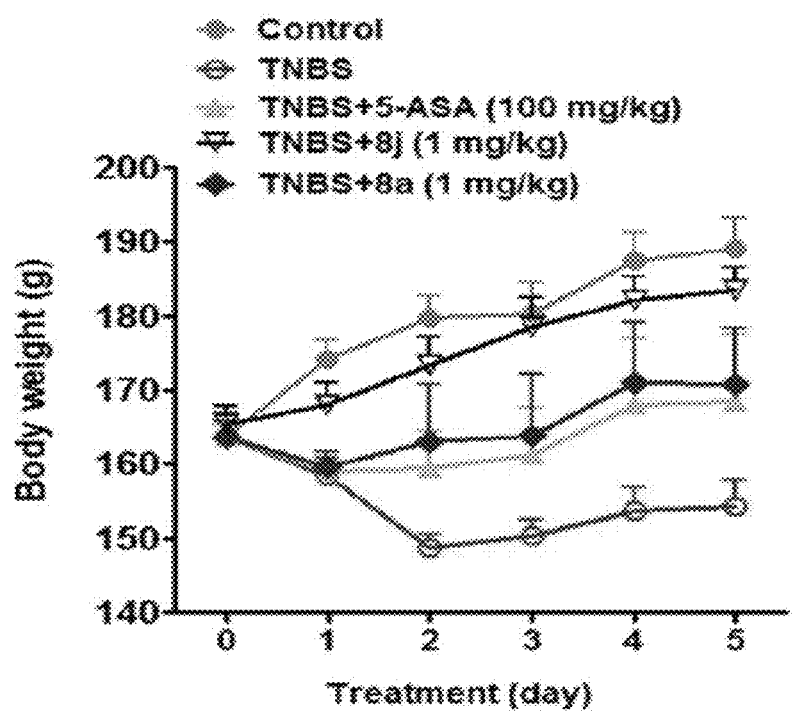
FIGS. 7 to 10 show results obtained by observing inhibitory effects of amidopyridinol derivatives against colitis in a rat induced with TNBS.
Figure 8:
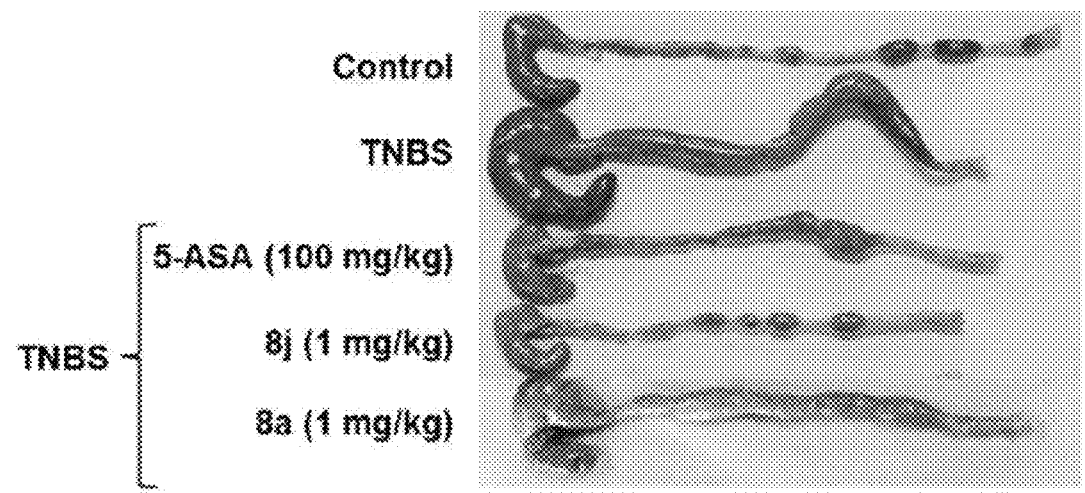
Figure 9:
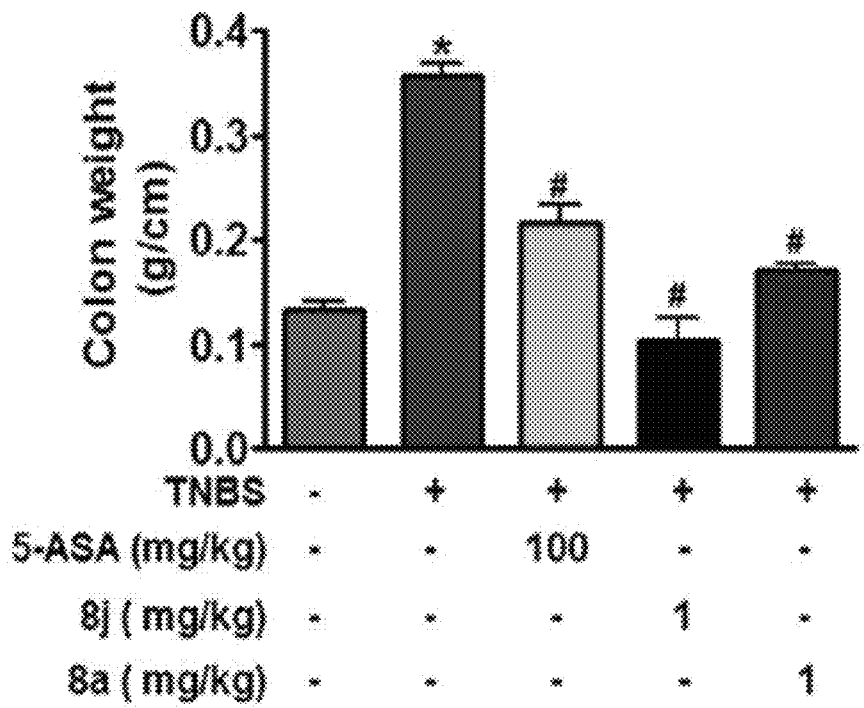
Figure 10:
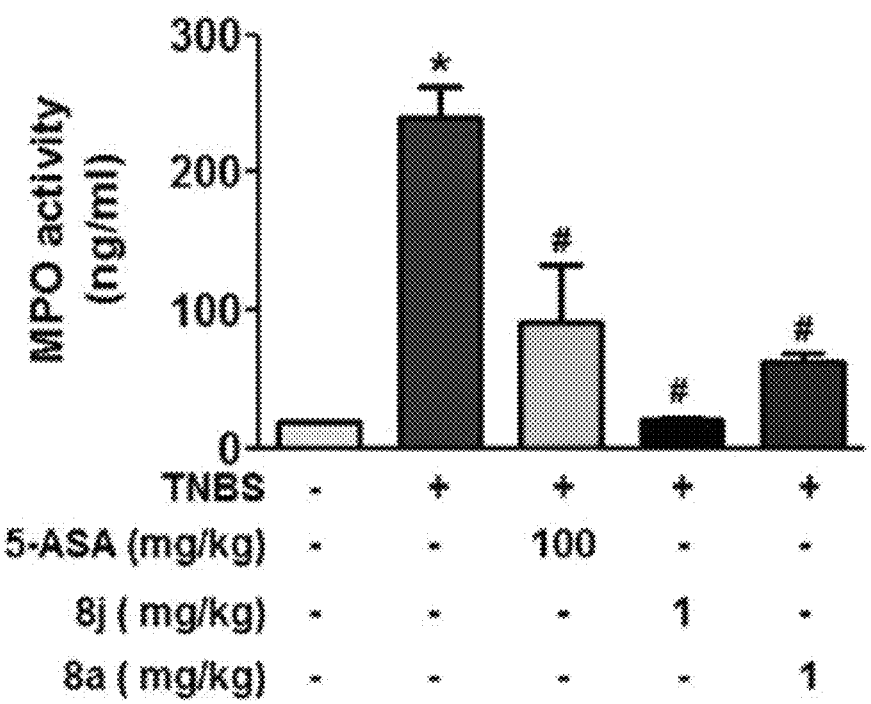

FIGS. 7 to 10 show effects of amidopyridinol compounds 8a and 8j on colitis of the TNBS-induced rats. FIG. 7 shows changes in weights of the rat as being recorded every day from the first day to the sixth day of the administration of test substances, FIG. 8 is a view showing conditions of a large intestine that was observed with the naked eye, FIG. 9 is a view showing weights of a large intestine, and FIG. 10 is a view showing measurement of the activation of MPO. Here, * indicates a case where a P value is smaller than 0.05 compared to a case where the rats were not treated with neither of drugs nor TNBS, and # indicates a case where a P value is smaller than 0.05 compared to a case where the rat was treated with TNBS.

As shown in FIG. 7, in an animal model with the rats having a weight ranging from about 180 g to about 190 g, having colitis, and causing intestinal inflammation by using 3% TNBS, changes in the weight were regularly observed for 5 days at a certain time. Based on the weight of the rats that were not treated with TNBS yet, it was confirmed that the control group treated with the vehicle continued to increase the weight of the rats, and the group treated with TNBS continued to decrease the weight of the rats, but was slightly recovered on the fifth day. However, the recovered weight of the TNBS-treated group was still significantly smaller than the weight of the rats in the normal group. The weight of the rats in the positive group that was treated with 300 mg/kg of 5-ASA was slowly recovered on the third day, and eventually, the rats in the positive group had greater weight than that of the rats in the group administered with TNBS only. The rats in the group treated with TNBS and administered with 1.0 mg/kg of Compound 8a showed a rapid increased in the weight thereof on the third day compared to the rats in the group treated with TNBS only, thereby eventually showing excellent recovery of the weight compared to the group treated with 5-ASA. In the case where 1.0 mg/kg of Compound 8j was administered to the rats, significant weight recovery and increased weight were instantly shown from the next day, thereby closely approaching the weight of the rats in the normal group.

FIG. 8 shows conditions of the large intestine that was harvested after the completion of the drug administration for 5 days5 and observed with the naked eye. Here, it was observed that the large intestine of the rats in the TNBS-treated group had swelling and redness, compared to that of the rats in the vehicle-treated normal group, and in addition, showed appendiceal swelling, congestion, and synechia. In the positive control group treated with 5-ASA (100 mg/kg), it was confirmed that symptoms that were observed with the naked eyes and synechia between other organs or inflamed large intestine was significantly inhibited compared to the group treated with TNBS only. That is, the group administered with Compounds 8a and 8j (1.0 mg/kg) exhibit excellent inhibitory effects on swelling and congestion.

In addition, FIG. 9 shows tissue weights measured after harvesting the large intestine of the rat, and it was confirmed that the group treated with TNBS only had a significant increase in the weight of the intestine having swelling, compared to the vehicle-treated normal group. In the positive control group treated with 5-ASA (100 mg/kg), it was confirmed that the intestine weight was significantly decreased compared to that of the TNBS-treated group. It was also observed that, in the group treated with Compounds 8a and 8j (1.0 mg/kg), the intestine weight was significantly decreased.

FIG. 10 is a graph showing the activity of MPO, wherein MPO is an enzyme mainly found in neutrophils. The activation of MPO in the tissue refers to an indicator of the invasion of neutrophils, and that is, the activation of MPO also refers to an indicator of inflammatory diseases, showing damaging levels in intestine upon inflammatory colitis and the correlation therebetween.

To measure the activation of MPO, an MPO assay was used. The colorectal tissue was washed with cold PBS, and a weight thereof was measured. Then, 200 μL of lysis buffer (pH7.4, 200 mM NaCl, 5 mM EDTA, 10 mM Tris, 10% glycerol) was added for each 10 mg of the weight of the tissue, and then, the tissue homogenizer (Bio homogenizer M133, BIOSPEC PRODUCTS Inc. USA) was used for 30 seconds in terms of homogenization. The homogenized sample was subjected to centrifugation (1500×g) twice, each for 15 minutes. The supernatant obtained therefrom was used to measure the activation of MPO by using the MPO ELISA kit (HK210, Hycult Biotechnology, Netherlands). 100 μL of the supernatant was added to the 96-well plates, each of which well was coated with an anti-mouse MPO antibody, to allow a reaction at room temperature for 1 hour, followed by being washed with PBS three times. Here, 100 μL of a reconstituted tracer was added thereto to allow a reaction at room temperature for 1 hour, followed by being washed three times repeatedly. Then, 100 μL of a reptavidin-peroxidase conjugate was added thereto to allow a reaction at room temperature for 1 hours, followed being washed. Then, 100 μL of a TMB substrate solution was added thereto to allow a reaction for 30 minutes. Then, 100 μL of a quiescent solution was added thereto to stop the reaction, and then, the absorbance was measured at a wavelength of 450 nm. The activation of MPO refers to levels at which 1 μM of hydrogen peroxide was reduced in water at a temperature of 25° C. for 1 minute, and the levels were calculated as the amount of MPO contained in 1 mL of the colorectal tissue homogenate. Here, * indicates a case where a P value is smaller than 0.05 compared to a case where the rats were not treated with neither of drugs nor TNBS, and # indicates a case where a P value is smaller than 0.05 compared to a case where the rat was treated with TNBS.

As shown in FIG. 10, it was confirmed that the group treated with TNBS only showed significantly increased activation of MPO, compared to that of the control group, and that the group administered with 5-ASA (100 mg/kg) showed significantly decreased activation of MPO compared to that of the control group. In addition, it was observed that the group treated with Compound 8a (1.0 mg/kg) showed lower activation of MPO compared to that of the group treated with TNBS only, thereby showing excellent effects in inhibiting activation of MPO in the colorectal tissue compared to the group treated with 5-ASA (100 mg/kg).

Experimental Example 6

Review of Inhibitory Effects on Angiogenesis and Tumor Growth by Tumorigenesis

To confirm inhibitory effects on angiogenesis through in vivo experiments, the CAM analysis was carried out (refer to Nguyen M et al., *Microvascular Res.*, 47, pp 31-40, 1994). A fertilized egg of a chicken was cultured in conditions maintaining a temperature of 37° C. and relative humidity of 55%. On the $9^{th}$ day of the culturing, a first small hole was made on an air sac part using a hypodermic needle (Green Cross Medical Corp., Korea), and then, a second hole was made on a flat part of the fertilized egg to make a window thereon. Air was removed through the first hole, i.e., the air sac part, and accordingly, the CAM was separated from the shell of the fertilized egg. Then, a grinding wheel (Multipro 395JA, Dremel, Mexico) was used to cut the air sac part, thereby making a window thereon. Meanwhile, A549 lung cancer cells were mixed with matrigel at a ratio of 1:1, and then, the mixture was treated with Compounds 8a, 8b, and 8g, respectively, followed by being inoculated at a density of $1.5 \times 10^6$ cells/CAM.

After 5 days of the inoculation, the CAM part on which tumors were formed was isolated, and then, washed with PBS. The Stemi SV6 stereomicroscope (Carl Zeiss, Germany) and the Image-Pro Plus software (Media Cybernetics; Silver Spring, Md., USA) were used to capture images of the CAM part, so as to measure the number of the blood vessels and to analyze data obtained therefrom.

Figure 11:
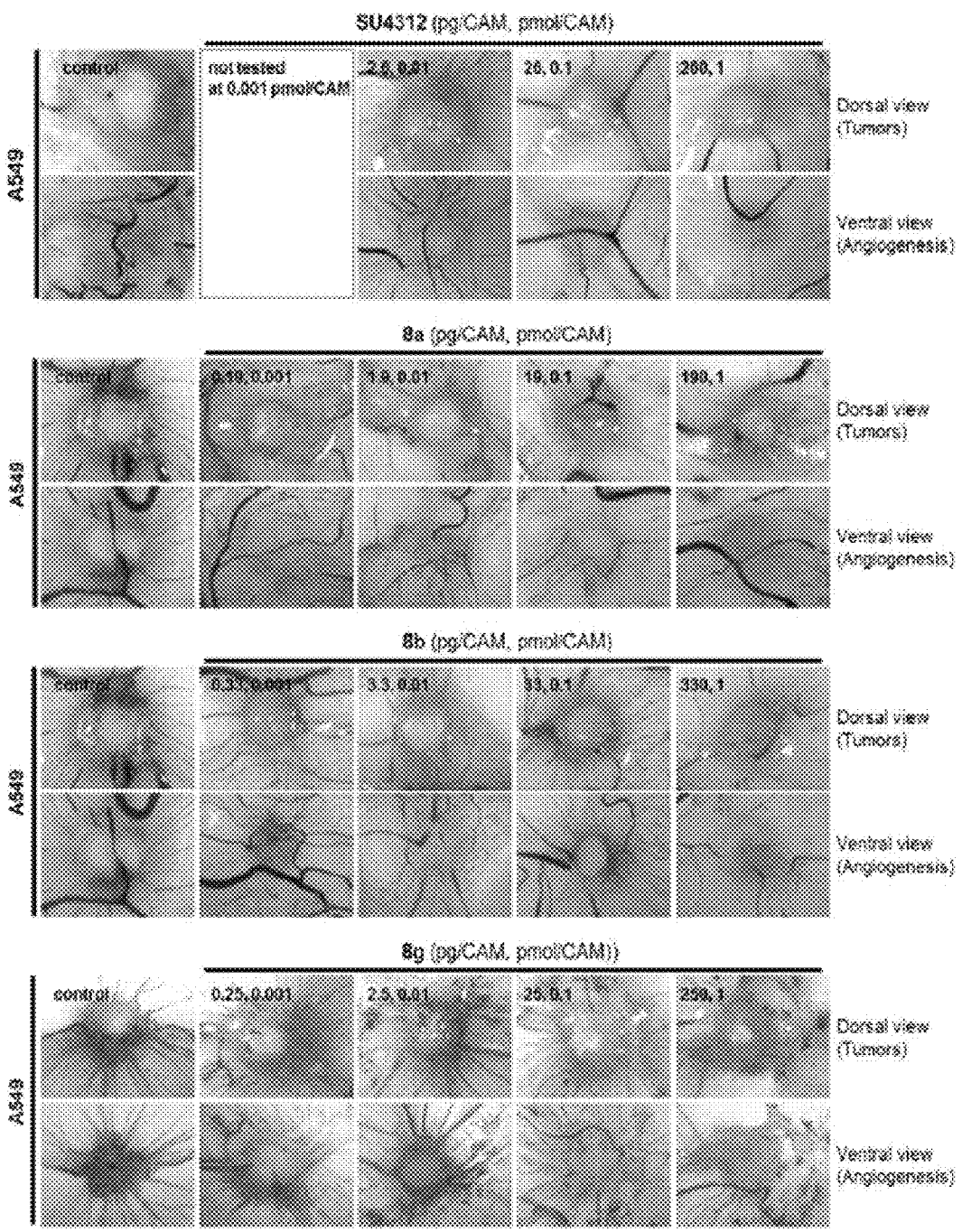
FIG. 11 is a view showing results obtained by observing inhibitory effects of Compounds 8a, 8b, and 8g on angiogenesis and tumor growth after inoculating a chorioallantoic membrane (CAM) with A549 lung cancer cells.

Consequently, as shown in Table 3 below and FIG. 11, it was confirmed that Compounds 8a, 8b, and 8g (at each density) inhibited angiogenesis upon tumorigenesis, as well as tumor growth.

TABLE 3

| Experimental groups | (pmol/CAM) | Inhibition rates of angiogenesis (%) | Inhibition rates of tumor growth (%) |
|---|---|---|---|
| SU4312 | 0.01 | 20.8 ± 1.4* | 16.2 ± 20.4 |
| SU4312 | 0.1 | 25.1 ± 2.8* | 23.4 ± 9.3 |
|  | 1.0 | 36.2 ± 1.9* | 26.8 ± 4.9 |
| 8a | 0.001 | 12.7 ± 6.5 | 20.3 ± 5.9 |
| 8a | 0.01 | 23.8 ± 5.2* | 34.2 ± 5.3* |
|  | 0.1 | 30.4 ± 3.7* | 37.9 ± 8.0* |
|  | 1.0 | 41.2 ± 1.4* | 47.7 ± 4.1* |
| 8b | 0.001 | 12.2 ± 4.4 | 21.7 ± 8.9 |
| 8b | 0.01 | 18.0 ± 3.2* | 26.0 ± 10.0 |
|  | 0.1 | 21.3 ± 2.0* | 31.3 ± 7.3* |
|  | 1.0 | 24.7 ± 2.2* | 38.2 ± 7.2* |
| 8g | 0.001 | 30.9 ± 8.5* | 13.2 ± 3.5 |
| 8g | 0.01 | 48.4 ± 4.1* | 24.0 ± 1.6* |
|  | 0.1 | 54.4 ± 6.7* | 45.1 ± 3.1* |
|  | 1.0 | 58.1 ± 6.8* | 62.7 ± 2.3* |

*$P < 0.05$ compared to the vehicle-treated group.

Experimental Example 7

Review of Inhibitory Effects on Invasion of Breast Cancer Cells by Using a Cathepsin Inhibitor To examine types of cathepsin serving an important role in invasion of metastatic breast cancer cells, e.g., MDA-MB-231, inhibitors including cathepsins B, D, K, L, and S were used to review inhibitory effects on invasion of breast cancer cells.

The invasion assay was performed by using the transwell insert (BD FALCON, Bedford, USA) equipped with a 8 μm pore-sized filter. An upper part of the transwell insert filter was coated with 20 μl of matrigel (1 mg/ml) while a bottom part of the same was coated with 30 μl of type I collagen (0.5 mg/ml). The MDA-MB-231 cells ($5 \times 10^5$ cells/100 μl) were added to the insert chamber, and then, each inhibitor was also added thereto. To induce invasion of the cells, a medium supplemented with 5% FBS was added to each well of the bottom chamber to allow a reaction at a temperature of 37° C. in a cell incubator. 18 hours later, the cells remained after removing the solution in the insert chamber were removed by using a cotton swab, whereas cells at the bottom of the membrane were fixed with methanol and stained with hematoxylin and eosin. The cells present at the membrane were observed through a microscope, and the number of the cells was counted in the selected 5 fields at the resolution of 200×.

Figure 12:
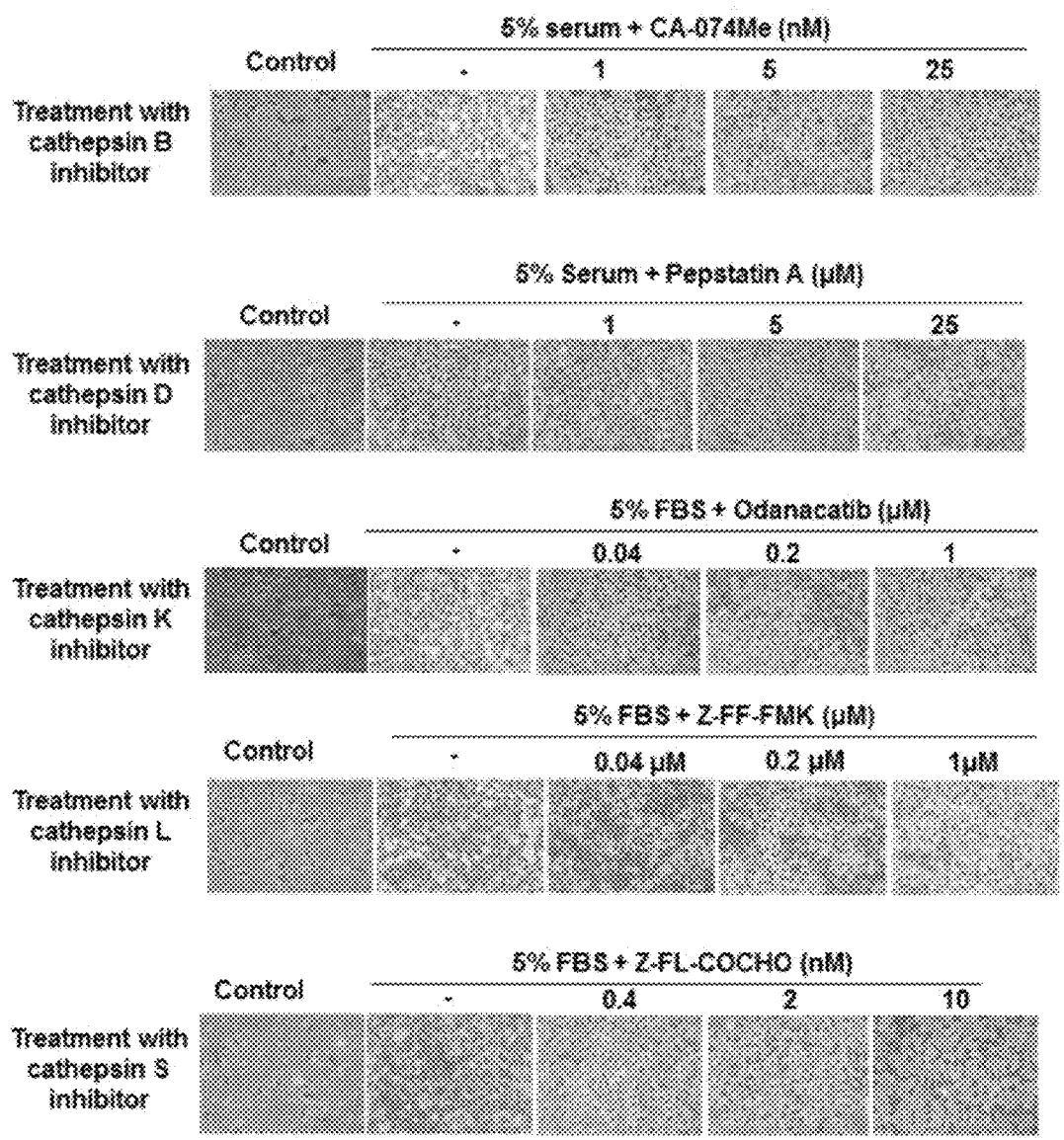
FIG. 12 is a view showing results obtained by observing inhibitory effects of a cathepsin inhibitor on invasion of MDA-MB-231 breast cancer cells.

Consequently, as shown in Table 4 below, the MDA-MB-231 cells that treated with cathepsin B inhibitor (CA-074 Me), cathepsin K inhibitor (Odanacatib), and cathepsin S inhibitor (Z-FL-COCHO) showed decreased invasion of the cells compared to the cells that were not treated with inhibitors. In particular, the MDA-MB-231 cells treated with cathepsin S inhibitor showed the most effective inhibition on invasion of the cells (refer to FIG. 12). Therefore, it was confirmed that cathepsin S serves an important role in terms of invasion of the breast cancer cells.

TABLE 4

| Types of cathepsin inhibitor | Concentration | Inhibition rates (%)* |
|---|---|---|
| CA-074 Me (cathepsin B inhibitor) | 1 nM | 19.73 ± 2.31# |
| CA-074 Me (cathepsin B inhibitor) | 5 nM | 34.26 ± 2.30# |
|  | 25 nM | 44.45 ± 1.43# |
| Pepstatin A (cathepsin D inhibitor) | 1 μM | 3.42 ± 0.42 |
| 펩스타틴 A (cathepsin D inhibitor) | 5 μM | 4.04 ± 0.33 |
|  | 25 μM | 5.54 ± 0.77 |
| Odanacatib (cathepsin K inhibitor) | 0.04 μM | 14.9 ± 4.14 |
| 오다나카팁 (cathepsin K inhibitor) | 0.2 μM | 19.95 ± 3.77# |
|  | 1 μM | 22.33 ± 3.70# |
| Z-FF-FMK (cathepsin L inhibitor) | 0.04 μM | 3.42 ± 2.08 |
| Z-FF-FMK (cathepsin L inhibitor) | 0.2 μM | 6.97 ± 2.35 |
|  | 1 μM | 10.16 ± 2.16# |
| Z-FL-COCHO (cathepsin S inhibitor) | 0.4 nM | 34.36 ± 3.00# |
| Z-FL-COCHO (cathepsin S inhibitor) | 2 nM | 44.67 ± 2.61# |
|  | 10 nM | 50.12 ± 2.76# |

*Percentage ± standard error in the number of cells reduced by an inhibitor
$P < 0.05$ compared to 5% FBS-treated group Experimental Example 8

Review of Inhibitory Effects of Amidopyridinol Derivatives on Invasion of MBA-MB-231 Cells According to the same manner as in Experimental Example 7, inhibitory effects of the amidopyridinol derivatives synthesized in Examples above on invasion of breast cancer cells, e.g., MDA-MB-231, were reviewed. Here, to compare with, inhibitory effects of aminopyridinol derivatives, e.g., 6-amino-2,4,5-trimethylpyridine-3-ol (BJ-1101) and 6-diphenylamino-2,4,5-trimethylpyridine-3-ol (BJ-1201), on invasion of breast cancer cells, e.g., MDA-MB-231, were reviewed.

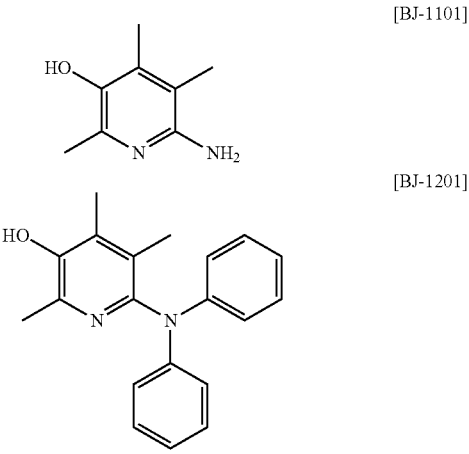

Consequently, as shown in Table 5 below, it was confirmed that the aminopyridinol derivatives, e.g., BJ-1101 and BJ-1201, had no inhibitory effects on invasion of breast cancer cells, e.g., MDA-MB-231, whereas Compounds 8l and 8q showed inhibitory effects on invasion of breast cancer cells, e.g., MDA-MB-231.

TABLE 5

| Compounds | Concentration (μM) | Inhibition rates of invasion of cancer cells (%)* |
|---|---|---|
| BJ-1101 | 0.01 | 0.45 ± 15.60 |
| BJ-1101 | 0.1 | 0 ± 17.25 |
|  | 1 | 0.30 ± 31.76 |
|  | 10 | 1.73 ± 22.66 |
| BJ-1201 | 0.01 | 2.52 ± 18.74 |
| BJ-1201 | 0.1 | 0 ± 19.27 |
|  | 1 | 1.78 ± 22.05 |
|  | 10 | 1.96 ± 6.78 |
| 8l | 0.01 | 8.57 ± 21.48 |
| 8l | 0.1 | 11.04 ± 23.06 |
|  | 1 | 33.04 ± 4.366# |
|  | 10 | 49.64 ± 7.82# |
| 8q | 0.01 | 47.59 ± 18.08# |
| 8q | 0.1 | 58.96 ± 10.42# |
|  | 1 | 65.77 ± 5.03# |
|  | 10 | 67.83 ± 4.25# |

*Percentage ± standard error in the number of cells reduced by the compound
P < 0.05 compared to 5% FBS-treated group Experimental Example 9

Review of Inhibitory Effects of Amidopyridinol Derivatives on Expression of Cathepsin S To review whether the amidopyridinol derivatives synthesized in Examples above had effects on expression of cathepsin S genes when treated with MDA-MB-231 cells, the RT-PCR was performed as follows.

Each compound of the present invention was treated with breast cancer cells ($1\times10^5$ cell/cm$^2$), e.g., MDA-MB-231, and then, cultured at a temperature of 37° C. for 24 hours in a cell incubator. Afterwards, a trizole reagent was used to extract the entire mRNA therefrom. 24 hours later, the culture medium was removed therefrom, 1 mL of the triazole reagent was added to each well, and then, the cell elusion was transferred to a 1.5 mL tube. After 200 μl of chloroform was added to each sample, the samples were subjected to centrifugation at a temperature of 4° C., at 12,000 g, for 15 minutes. 500 μl of the supernatant obtained therefrom was transferred to a new tube. After 500 μl of isopropylalcohol was added to each sample, the samples were subjected to centrifugation at a temperature of 4° C., at 12,000 g, for 15 minutes. The supernatant obtained therefrom was removed from each sample, and then, the samples were washed with 75% ethanol to clean mRNA while the precipitants were dried. Then, mRNA extracted therefrom was dissolved in RNase-free water, followed by being heated at a temperature of 55° C. for 10 minutes.

After the RNA quantification, the GoScript™ reverse transcription system (Promega Corporation, Madison, Wis., USA) was used to synthesize cDNA. Here, PCR was performed by using TaKaRa Taq™ (Takara bio Inc., Shiga, Japan), wherein a primer set of cathepsin S consists of a forward primer having SEQ ID NO: 1 (forward sequence: 5'-GCA GTG GCA CAG TTG CAT AA-3') and a reverse primer having SEQ ID NO: 2 (reverse sequence: 5'-AGC ACC ACA AGA ACC CAT GT-3'). After the PCR product was subjected to agarose gel electrophoresis, the PCR product was stained with ethidium bromide (0.5 μg/ml), thereby obtaining images thereof by using the gel imaging system (UVP, Cambridge, UK). Here, the PCR product was quantified based on glyceraldehyde 3-phosphate dehydrogenase (GAPDH). A GAPDH primer used herein consists of a forward primer having SEQ ID NO: 3 (forward sequence: 5'-GGT GAA GGT CGG AGT CAA CG-3') and a reverse primer having SEQ ID NO: 4 (reverse sequence: 5'-CAA AGT TGT CAT GGA TGA CC-3').

Consequently, as shown in Table 6, it was confirmed that BJ-1101 and BJ-1201, which had no inhibitory effects on invasion of MDA-MB-231 cells, both had no effects for reducing expression of cathepsin S genes. In addition, it was confirmed that Compound 8q, which had shown the most inhibitory effects on invasion of cancer cells, also had the most effects for reducing expression of cathepsin S genes. Therefore, it was confirmed that inhibitory effects on invasion of MDA-MB-231 cells and inhibitory effects on expression of cathepsin S genes are very significantly related to each other.

TABLE 6

| Compound | Concentration (μM) | Inhibition rate of expression of cathepsin S (%)* |
|---|---|---|
| BJ-1101 | 1 | 3.3 ± 0.82 |
| BJ-1201 | 1 | 2.7 ± 0.12 |
| 8l | 1 | 0 ± 0.17 |
| 8l | 10 | 12 ± 0.35 |
| 8q | 0.01 | 42 ± 1.21 |
| 8q | 0.1 | 52 ± 1.68 |
|  | 1 | 57 ± 1.55 |

*Percentage ± standard error in the number of cells reduced by the compound based on PCR band (control group) that was not treated with the compound Experimental Example 10

Screening of Compounds that Inhibit Expression of Cathepsin S in Breast Cancer Cells, e.g., MDA-MB-231

As described in previous Experimental Examples, it was confirmed that cathepsin S had an important role in invasion of breast cancer cells, e.g., MDA-MB-231. Furthermore, to screen other amidopyridinol derivatives that inhibit metastasis of breast cancer cells, inhibitory effects on expression of cathepsin S genes were reviewed by treating 1 μM of each compound, in the same manner as in Experimental Example 9.

Consequently, as shown in Table 7, Compounds 8a, 8b, and 8g were found to have inhibitory effects on expression of cathepsin S genes, and that is, these compounds had inhibition rates of 50% or more. Thus, it was conformed that these compounds had excellent inhibitory effects on invasion of metastatic breast cancer cells.

TABLE 7

| Compound | Inhibition rate of expression of cathepsin S (%)* |
|---|---|
| 8a | 56 ± 0.21 |
| 8b | 55 ± 0.35 |
| 8c | 27 ± 1.33 |
| 8d | 33 ± 1.23 |
| 8f | 16.4 ± 0.12 |
| 8g | 60.4 ± 3.55 |
| 8n | 8 ± 0.41 |
| 8p | 44 ± 2.47 |

TABLE 7-continued

| Compound | Inhibition rate of expression of cathepsin S (%)* |
|---|---|
| 8r | 3.9 ± 0.22 |
| 8s | 4.2 ± 0.31 |
| 8t | 8.2 ± 0.43 |
| 8u | 2.9 ± 0.08 |

*Percentage ± standard error in the number of cells reduced by the compound based on PCR band (control group) that was not treated with the compound Experimental Example 11

Toxicity Test

In male Balb/c mice, Compound 8a was suspended with 0.5% methyl cellulose solution at different amounts of 0.5 g/kg, 1 g/kg, and 2 g/kg. Here, only one single oral administration was performed, and then, the survival rates and weight of the mice were observed for 7 days.

After such administration, the mortality, clinical symptoms, and changes in weight of the animals were observed. The animals were subjected to hematological and blood biochemical tests, and to autopsy, thereby observing any abnormality in abdominal organs and thoracic organs.

Consequently, it was confirmed that all the animals had no particular clinical symptoms or mortality, and in addition, no toxic changes were found in terms of the changes in the weight, blood test, blood biochemical test, and sutopsy.

Hereinabove, the compounds of the present invention did not exhibit any toxic changes in mice weighing up to 2 g/kg, and thus, it was determined that the compounds of the present invention were safe substances since a median lethal dose (LD50) of the oral administration was at least 2 g/kg.

Hereinafter, methods of preparing compositions including Compound 8a according to the present invention are described in connection with Preparation Examples. However, be understood that these examples are only used to specifically set forth the present disclosure, and they are not limited in any form.

Preparation Example 1

Preparation of Powders 20 mg of Compound 8a, 100 mg of lactose, and 10 mg of talc were mixed together, and then, the mixture was filled in airtight to prepare posers.

Preparation Example 2

Preparation of Tablets 20 mg of Compound 8a, 100 mg of corn starch, 100 mg of lactose, and 2 mg of magnesium stearate were mixed together, and then, the mixture was prepared compressed according to convention methods known in the art to prepare tablets.

Preparation Example 3

Preparation of Capsules 10 mg of Compound 8a, 100 mg of corn starch, 100 mg of lactose, and 2 mg of magnesium stearate were mixed together according to convention methods known in the art, and then, the mixture was filled in gelatin capsules to prepare capsules.

Preparation Example 4

Preparation of Injections 10 mg of Compound 8a and appropriate amounts of sterilized distilled water for injection and pH adjustor were mixed together, and then, the mixture was prepared to have 2 ml per ample according to the conventional preparation method for injections known in the art.

Preparation Example 5

Preparation of Ointment 10 mg of Compound 8a, 250 mg of PEG-4000, 650 mg of PEG-400, 10 mg of white vaseline, 1.44 mg of methyl ρ-hydroxybenzoate, 0.18 mg of propyl ρ-hydroxybenzoate, and the remaining amounts of purified water were mixed together, and then, the mixture was prepared as ointment according to convention preparation method for ointment.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

The invention claimed is:

1. A compound represented by Chemical Formula 1 below or a pharmaceutically acceptable salt thereof:

[Chemical Formula 1]

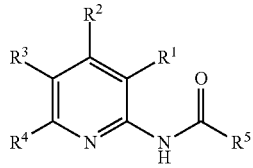

wherein, in Chemical Formula 1 above, $R^1$, $R^2$, and $R^4$ are identical to or different from each other, and are each independently one selected from hydrogen, C1-C4 alkyl, and C1-C4 alkoxy, wherein hydrogen is not simultaneously selected by $R^1$, $R^2$, and $R^4$, $R^3$ is one selected from benzyloxy and hydroxy, and $R^5$ is one selected from C1-C15 alkyl substituted or not substituted with one or two substituents selected from halogen, hydroxy, C1-C12 alkoxy, phenoxy, C1-C12 alkylamino, C6-C14 aryl, and C1-C4 alkyl; C6-C14 aryl substituted or not substituted with one or two substituents selected from halogen, hydroxy, C1-C12 alkoxy, C1-C12 alkylamino, and C1-C4 alkyl; C2-C12 alkenyl substituted or not substituted with C6-C14 aryl; C3-C8 cycloalkyl; a 5- to 6-membered monocyclic heterocyclic compound containing one or two heteroatoms from N, S, or O; a heterocyclic compound containing a double ring structure having the 5- to 6-membered monocyclic heterocyclic compound and a phenyl; and naphthalene.

2. The compound or the pharmaceutically acceptable salt thereof of claim 1, wherein in the compound of Chemical Formula 1, $R^1$, $R^2$, and $R^4$ are each independently one selected from hydrogen, C1-C4 alkyland C1-C4 alkoxy, wherein hydrogen is not simultaneously selected by $R^1$, $R^2$, and $R^4$, $R^3$ is one selected from benzyloxy and hydroxy, and $R^5$ is selected from C1-C15 alkyl substituted or not substituted with one selected from halogen and C1-C4 alkyl; phenyl substituted with or not substituted with one selected from halogen, hydroxy, C1-C4 alkoxy, and C1-C4 alkyl; C1-C4 alkyl substituted with phenyl or halophenylene; cinnamyl; phenoxymethylene; C3-C8 cycloalkyl; benzodioxole; naphthalene; and thiophene.

3. The compound or the pharmaceutically acceptable salt thereof of claim 1, wherein the compound is one selected from a N-(5-benzyloxy-3,4,6-trimethylpyridine-2-yl)amide and a N-(5-hydroxy-3,4,6-trimethylpyridine-2-yl)amide.

4. The compound or the pharmaceutically acceptable salt thereof of claim 3, wherein the N-(5-benzyloxy-3,4,6-trimethylpyridine-2-yl)amide is one selected from N -(5-benzyloxy-3,4,6-trimethylpyridine-2-yl)acetamide, N-(5-benzyloxy-3,4,6-trimethylpyridine-2-yl) dodecanamide, N-(5-benzyloxy-3,4,6-trimethylpyridine-2-yl)-4-chlorobutanamide, N-(5-benzyloxy-3 ,4,6-trimethylpyridine-2-yl)isobutyrylamide, N-(5-benzyloxy-3,4,6-trimethylpyridine-2-yl)-3-methylbutanamide, N-(5-benzyloxy-3,4,6-trimethylpyridine-2-yl)pivalamide, N-(5-benzyloxy-3,4,6-trimethylpyridine-2-yl) cyclopentanecarboxamide N-(5-benzyloxy-3,4,6-trimethylpyridine-2-yl)cyclohexanecarboxamide N-(5-benzyloxy-3,4,6-trimethylpyridine-2-yl)-2-penylacetamide, N-(5-benzyloxy-3,4,6-trimethylpyridine-2-yl)-3-phenylpropanamide, N-(5-benzyloxy-3,4,6-trimethylpyridine-2-yl) benzamide, N-(5-benzyloxy-3,4,6-trimethylpyridine-2-yl)-4-fluorobenzamide, N-(5-benzyloxy-3,4,6-trimethylpyridine-2-yl)-4-methoxybenzamide, N-(5-benzyloxy-3,4,6-trimethylpyridine-2-yl)-4-(tert-butyl)benzamide, N-(5-benzyloxy-3,4,6-trimethylpyridine-2-yl)benzo[d][1,3] dioxo1-5-carboxamide, N-(5-benzyloxy-3,4,6-trimethylpyridine-2-yl)-1-naphthamide, N-(5-benzyloxy-3,4,6-trimethylpyridine-2-yl)thiophene-2-carboxamide, N-(5-benzyloxy-3,4,6-trimethylpyridine-2-yl)-2-ethylbutanamide, N-(5-benzyloxy-3,4,6-trimethylpyridine-2-yl)-2-phenoxyacetamide, N-(5-benzyloxy-3,4,6-trimethylpyridine-2-yl)-2-phenylbutanamide, N-(5-benzyloxy-3,4,6-trimethylpyridine-2-yl)-2,4,6-trimethylbenzamide, 3-benzyloxy-N-(5-benzyloxy-3,4,6-trimethylpyridine-2-yl)benzamide, N-(5-benzyloxy-3,4,6-trimethylpyridine-2-yl)-3,5,5-trimethylhexanamide, N-(5-benzyloxy-3,4,6-trimethylpyridine-2-yl)-2-(4-chlorophenyl)acetamide, N-(5-benzyloxy-3,4,6-trimethylpyridine-2-yl)-2,2-dichloroacetamide, and N-(5-benzyloxy-3,4,6-trimethylpyridine-2-yl)cinnamide.

5. The compound or the pharmaceutically acceptable salt thereof of claim 3, wherein the N-(5-hydroxy-3,4,6-trimethylpyridine-2-yl)amide is one selected from N -(5-hydroxy-3,4,6-trimethylpyridine-2-yl)acetamide, N-(5-hydroxy-3,4,6-trimethylpyridine-2-yl)dodecanamide, N-(5-hydroxy-3,4,6-trimethylpyridine-2-yl)-4-chlorobutanamide, N-(5-hydroxy-3,4,6-trimethylpyridine-2-yl)isobutyrylamide, N-(5-hydroxy-3,4,6-trimethylpyridine-2-yl)-3-methylbutanamide, N-(5-hydroxy-3,4,6-trimethylpyridine-2-yl)pivalamide, N-(5-hydroxy-3,4,6-trimethylpyridine-2-yl)cyclopentanecarboxamide, N-(5-hydroxy-3,4,6-trimethylpyridine-2-yl)cyclohexanecarboxamide, N-(5-hydroxy-3,4,6-trimethylpyridine-2-yl)-2-penylacetamide, N-(5-hydroxy-3,4,6trimethylpyridine-2-yl)-3-phenylpropanamide, N-(5-hydroxy-3,4,6-trimethylpyridine-2-yl)benzamide, N-(5-hydroxy-3,4,6-trimethylpyridine-2-yl)-4-fluorobenzamide, N-(5-hydroxy-3,4,6-trimethylpyridine-2-yl)-4-methoxybenzamide, N-(5-hydroxy-3,4,6-trimethylpyridine-2-yl)-4-(tert-butyl)benzamide, N-(5-hydroxy-3,4,6-trimethylpyridine-2-yl)benzo[d][1,3]dioxo1-5-carboxamide, N-(5-hydroxy-3,4,6-trimethylpyridine-2-yl)-1-naphthamide, N-(5-hydroxy-3,4,6-trimethylpyridine-2-yl)thiophene-2-carboxamide, 2-ethyl-N-(5-hydroxy-3,4,6-trimethylpyridine-2-yl)butanamide, N-(5-hydroxy-3,4,6-trimethylpyridine-2-yl)-2-phenoxyacetamide, N-(5-hydroxy-3,4,6-trimethylpyridine-2-yl)-2-phenylbutanamide, N-(5-hydroxy-3,4,6-trimethylpyridine-2-yl)-2,4,6-trimethylbenzamide, 3-hydroxy-N-(5-hydroxy-3,4,6-trimethylpyridine-2-yl)benzamide, N-(5-hydroxy-3,4,6-trimethylpyridine-2-yl)-3,5,5-trimethylhexanamide, 2-(4-chlorophenyl)-N-(5-hydroxy-3,4,6-trimethylpyridine-2-yl)acetamide, 2,2- dichloro-N-(5-hydroxy-3,4,6-trimethylpyridine-2-yl)acetamide, and N-(5-hydroxy-3,4,6-trimethylpyridine-2-yl)cinnamide.

6. The compound or the pharmaceutically acceptable salt thereof of claim 1, wherein the pharmaceutically acceptable salt is an organic acid selected from oxalic acid, maleic acid, fumaric acid, malic acid, tartaric acid, citric acid, and benzoic acid, or is in a form of acid addition formed by an inorganic acid selected from hydrochloric acid, sulfuric acid, phosphoric acid, and hydrobromic acid.

7. A method of treating an inflammatory bowel disease in a subject in need thereof, comprising:

administering an effective amount of a compound represented by Chemical Formula 2 or a pharmaceutically acceptable salt thereof to the subject,

[Chemical Formula 2]

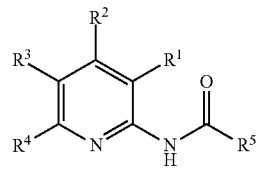

wherein, in Chemical Formula 2 above, $R^1$, $R^2$, and $R^4$ are identical to or different from each other, and are each independently one selected from hydrogen, C1-C4 alkyl, C1-C4 alkoxy, and halogen, $R^3$ is one selected from C1-C4 alkoxy, benzyloxy, and hydroxyl, and, $R^5$ is one selected from C1-C15 alkyl substituted or not substituted with one or two substituents selected from halogen, hydroxy, C1-C12 alkoxy, phenoxy, C1-C12 alkylamino, C6-C14aryl, and C1-C4 alkyl; C6-C14 aryl substituted or not substituted with one or two substituents selected from halogen, hydroxy, C1-C12 alkoxy, C1-C12 alkylamino, and C1-C4alkyl; C2-C12 alkenyl substituted or not substituted with C6-C14 aryl; C3-C8 cycloalkyl; a 5- to 6-membered monocyclic heterocyclic compound containing one or two heteroatoms selected from N, S or O; a heterocyclic compound containing a double ring structure having the 5- to 6-membered monocyclic heterocyclic compound and a phenyl; and naphthalene.

8. The method of claim 7, wherein the inflammatory bowel disease is one selected from ulcerative colitis, Crohn's disease, intestinal Behcet's disease, hemorrhagic rectal ulcer, and pouchitis.

9. A method of treating a lung or breast cancer in a subject in need thereof, comprising:
administering an effective amount of a compound represented by Chemical Formula 2 or a pharmaceutically acceptable salt thereof to the subject,

[Chemical Formula 2]

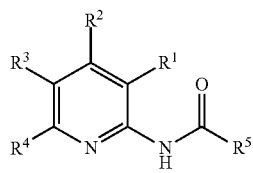

wherein, in Chemical Formula 2 above,
$R^1$, $R^2$, and $R^4$ are identical to or different from each other, and are each independently one selected from hydrogen, C1-C4 alkyl, C1-C4 alkoxy, and halogen,
$R^3$ is one selected from C1-C4 alkoxy, benzyloxy, and hydroxyl, and
$R^5$ is one selected from C1-C15 alkyl substituted or not substituted with one or two substituents selected from halogen, hydroxy, C1-C12 alkoxy, phenoxy, C1-C12 alkylamino, C6-C14 aryl, and C1-C4 alkyl; C6-C14 aryl substituted or not substituted with one or two substituents selected from halogen, hydroxy, C1-C12 alkoxy, C1-C12 alkylamino, and C1-C4 alkyl; C2-C12 alkenyl substituted or not substituted with C6-C14 aryl; C3-C8 cycloalkyl; a 5- to 6-membered monocyclic heterocyclic compound containing one or two heteroatoms selected from N, S or O; a heterocyclic compound containing a double ring structure having the 5- to 6-membered monocyclic heterocyclic compound and a phenyl; and naphthalene,
wherein the compound inhibits invasion of cancer or metastasis.

* * * * *